United States Patent
Azorsa

(10) Patent No.: US 9,738,717 B2
(45) Date of Patent: Aug. 22, 2017

(54) HYBRIDOMA CLONES, MONOCLONAL ANTIBODIES, AND METHODS OF USE

(71) Applicant: The Translational Genomics Research Institute, Phoenix, AZ (US)

(72) Inventor: David Azorsa, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 0 days.

(21) Appl. No.: 14/890,317

(22) PCT Filed: May 15, 2013

(86) PCT No.: PCT/US2013/041256
§ 371 (c)(1),
(2) Date: Nov. 10, 2015

(87) PCT Pub. No.: WO2014/185908
PCT Pub. Date: Nov. 20, 2014

(65) Prior Publication Data
US 2016/0115229 A1    Apr. 28, 2016

(51) Int. Cl.
*A61K 39/395* (2006.01)
*C07K 16/28* (2006.01)
*C07K 16/30* (2006.01)
*G01N 33/574* (2006.01)

(52) U.S. Cl.
CPC .......... *C07K 16/28* (2013.01); *C07K 16/2896* (2013.01); *C07K 16/3046* (2013.01); *G01N 33/57492* (2013.01); *G01N 2333/705* (2013.01)

(58) Field of Classification Search
None
See application file for complete search history.

(56) References Cited

FOREIGN PATENT DOCUMENTS

| WO | WO 2005/092377 | 10/2005 |
|---|---|---|
| WO | WO 2011/029823 | 3/2011 |
| WO | WO 2011/066589 | 6/2011 |

OTHER PUBLICATIONS

George et al. (Circulation. 1998; 97: 900-906).*
Azorsa, et al. A General Approach to the Generation of Monoclonal Antibodies Against Members of the Tetraspanin . . . Journal of Immunilogical Methods 1999, 229(1-3):35-48; Abstr.
International Search Report and Written Opinion, PCT Application Serial No. PCT/US2013/041256.

* cited by examiner

*Primary Examiner* — Sheela J Huff
(74) *Attorney, Agent, or Firm* — Rodney J. Fuller; Booth Udall Fuller, PLC

(57) ABSTRACT

The present invention is directed to a monoclonal antibody that recognizes human CD63 in its native form. The invention is also directed to a hybridoma cell line that produces the monoclonal antibody, and to methods of diagnosing and treating cancer and purifying exosomes using the antibody. The invention is further directed to pharmaceutical compositions comprising an antibody of the invention and a pharmaceutically acceptable carrier.

15 Claims, 21 Drawing Sheets

|   | 1 | 2 | 3 | 4 | 5 | 6 | 7 | 8 | 9 | 10 | 11 | 12 | 13 |
|---|---|---|---|---|---|---|---|---|---|---|---|---|---|
| A | 1.397 | 0.134 | 0.115 | 0.142 | 0.127 | 0.101 | 0.099 | 0.146 | 0.096 | 0.098 | 0.147 | 0.105 | 0.129 |
| B | 0.169 | 0.126 | 0.093 | 0.091 | 0.093 | 0.095 | 0.116 | 0.103 | 0.1 | 0.1 | 0.095 | 0.103 | 0.098 |
| C | 0.066 | 0.072 | 0.072 | 0.077 | 0.074 | 0.076 | 0.078 | 0.113 | 0.077 | 0.223 | 0.089 | 0.089 | 0.088 |
| D | 0.139 | 0.089 | 0.086 | 0.09 | 0.107 | 0.094 | 0.093 | 0.097 | 0.087 | 0.092 | 0.089 | 0.092 | 0.096 |
| E | 0.069 | 0.08 | 0.074 | 0.073 | 0.075 | 0.074 | 0.079 | 0.084 | 0.145 | 0.074 | 0.107 | 0.094 | 0.089 |
| F | 0.115 | 0.093 | 0.086 | 0.086 | 0.082 | 0.095 | 0.088 | 0.091 | 0.085 | 0.083 | 0.088 | 0.123 | 0.089 |
| G | 0.077 | 0.071 | 0.072 | 0.09 | 0.078 | 0.074 | 0.075 | 0.117 | 0.078 | 0.09 | 0.093 | 0.092 | 0.095 |
| H | 0.134 | 0.104 | 0.095 | 0.095 | 0.096 | 0.097 | 0.1 | 0.11 | 0.097 | 0.097 | 0.097 | 0.106 | 0.097 |
| I | 0.068 | 0.081 | 0.112 | 0.077 | 0.076 | 0.074 | 0.083 | 0.088 | 0.076 | 0.088 | 0.08 | 0.086 | 0.085 |
| J | 0.114 | 0.087 | 0.086 | 0.096 | 0.081 | 0.084 | 0.084 | 0.091 | 0.088 | 0.09 | 0.084 | 0.086 | 0.089 |
| K | 0.069 | 0.071 | 0.071 | 0.07 | 0.074 | 0.068 | 0.097 | 0.079 | 0.071 | 0.078 | 0.078 | 0.082 | 0.084 |
| L | 0.12 | 0.088 | 0.098 | 0.091 | 0.085 | 0.083 | 0.103 | 0.095 | 0.093 | 0.102 | 0.095 | 0.091 | 0.089 |
| M | 0.083 | 0.092 | 0.088 | 0.288 | 0.069 | 0.072 | 0.079 | 0.089 | 0.075 | 0.072 | 0.079 | 0.083 | 0.101 |
| N | 0.177 | 0.091 | 0.086 | 0.084 | 0.095 | 0.082 | 0.087 | 0.085 | 0.087 | 0.083 | 0.085 | 0.084 | 0.086 |
| O | 0.106 | 0.096 | 0.08 | 0.079 | 0.074 | 0.079 | 0.09 | 0.078 | 0.079 | 0.084 | 0.086 | 0.088 | 0.089 |
| P | 0.655 | 0.147 | 0.163 | 0.139 | 0.171 | 0.12 | 0.107 | 0.135 | 0.117 | 0.115 | 0.1 | 0.112 | 0.186 |

FIG. 2A

|   | 14 | 15 | 16 | 17 | 18 | 19 | 20 | 21 | 22 | 23 | 24 | Max Value |
|---|---|---|---|---|---|---|---|---|---|---|---|---|
| A | 0.103 | 0.124 | 0.099 | 0.1 | 0.107 | 0.103 | 0.099 | 0.107 | 0.122 | 0.136 | 0.228 | 1.707 |
| B | 0.097 | 0.094 | 0.094 | 0.093 | 0.093 | 0.093 | 0.101 | 0.14 | 0.159 | 0.174 | 0.29 | |
| C | 0.087 | 0.09 | 0.088 | 0.084 | 0.086 | 0.102 | 0.085 | 0.081 | 0.082 | 0.086 | 0.195 | |
| D | 0.095 | 0.091 | 0.093 | 0.095 | 0.092 | 0.099 | 0.093 | 0.114 | 0.134 | 0.147 | 0.214 | |
| E | 0.081 | 0.08 | 0.404 | 0.081 | 0.085 | 0.085 | 0.079 | 0.079 | 0.09 | 0.078 | 0.201 | |
| F | 0.093 | 0.09 | 0.115 | 0.088 | 0.093 | 0.094 | 0.087 | 0.113 | 0.134 | 0.126 | 0.236 | |
| G | 0.09 | 0.095 | 0.095 | 0.097 | 0.098 | 0.125 | 0.095 | 0.09 | 0.094 | 0.095 | 0.185 | |
| H | 0.105 | 0.101 | 0.097 | 0.101 | 0.1 | 0.102 | 0.109 | 0.14 | 0.189 | 0.223 | 0.253 | |
| I | 0.091 | 0.086 | 0.085 | 0.088 | 0.089 | 0.098 | 0.093 | 0.156 | 0.09 | 0.121 | 0.147 | |
| J | 0.103 | 0.086 | 0.091 | 0.087 | 0.272 | 0.105 | 0.09 | 0.087 | 0.106 | 0.176 | 0.206 | |
| K | 0.088 | 0.085 | 0.094 | 0.09 | 0.085 | 0.087 | 0.083 | 0.08 | 0.097 | 0.158 | 0.207 | |
| L | 0.091 | 0.088 | 0.086 | 0.089 | 0.086 | 0.099 | 0.087 | 0.098 | 0.14 | 0.219 | 0.296 | |
| M | 0.127 | 0.084 | 0.081 | 0.08 | 0.285 | 0.083 | 0.081 | 0.08 | 0.11 | 0.303 | 0.313 | |
| N | 0.087 | 0.088 | 0.089 | 0.097 | 0.104 | 0.111 | 0.094 | 0.102 | 0.151 | 0.412 | 0.31 | |
| O | 0.09 | 0.095 | 0.096 | 0.119 | 0.136 | 0.114 | 0.097 | 0.099 | 0.277 | 0.434 | 0.436 | |
| P | 0.141 | 0.117 | 0.176 | 0.143 | 0.202 | 0.187 | 0.144 | 0.185 | 0.378 | 1.707 | 0.53 | |

FIG. 2A (cont'd)

|   | 1 | 2 | 3 | 4 | 5 | 6 | 7 | 8 | 9 | 10 | 11 | 12 | 13 |
|---|---|---|---|---|---|---|---|---|---|---|---|---|---|
| A | 81.8 | 7.9 | 6.7 | 8.3 | 7.4 | 5.9 | 5.8 | 8.6 | 5.6 | 5.7 | 8.6 | 6.2 | 7.6 |
| B | 9.9 | 7.4 | 5.4 | 5.3 | 5.4 | 5.6 | 6.8 | 6.0 | 5.9 | 5.9 | 5.6 | 6.0 | 5.7 |
| C | 3.9 | 4.2 | 4.2 | 4.5 | 4.3 | 4.5 | 4.6 | 6.6 | 4.5 | 13.1 | 5.2 | 5.2 | 5.2 |
| D | 8.1 | 5.2 | 5.0 | 5.3 | 6.3 | 5.5 | 5.4 | 5.7 | 5.1 | 5.4 | 5.2 | 5.4 | 5.6 |
| E | 4.0 | 4.7 | 4.3 | 4.3 | 4.4 | 4.3 | 4.6 | 4.9 | 8.5 | 4.3 | 6.3 | 5.5 | 5.2 |
| F | 6.7 | 5.4 | 5.0 | 5.0 | 4.8 | 5.6 | 5.2 | 5.3 | 5.0 | 4.9 | 5.2 | 7.2 | 5.2 |
| G | 4.5 | 4.2 | 4.2 | 5.3 | 4.6 | 4.3 | 4.4 | 6.9 | 4.6 | 5.3 | 5.4 | 5.4 | 5.6 |
| H | 7.9 | 6.1 | 5.6 | 5.6 | 5.6 | 5.7 | 5.9 | 6.4 | 5.7 | 5.7 | 5.7 | 6.2 | 5.7 |
| I | 4.0 | 4.7 | 6.6 | 4.5 | 4.5 | 4.3 | 4.9 | 5.2 | 4.5 | 5.2 | 4.7 | 5.0 | 5.0 |
| J | 6.7 | 5.1 | 5.0 | 5.6 | 4.7 | 4.9 | 4.9 | 5.3 | 5.2 | 5.3 | 4.9 | 5.0 | 5.2 |
| K | 4.0 | 4.2 | 4.2 | 4.1 | 4.3 | 4.0 | 5.7 | 4.6 | 4.2 | 4.6 | 4.6 | 4.8 | 4.9 |
| L | 7.0 | 5.2 | 5.7 | 5.3 | 5.0 | 4.9 | 6.0 | 5.6 | 5.4 | 6.0 | 5.6 | 5.3 | 5.2 |
| M | 4.9 | 5.4 | 5.2 | 16.9 | 4.0 | 4.2 | 4.6 | 5.2 | 4.4 | 4.2 | 4.6 | 4.9 | 5.9 |
| N | 10.4 | 5.3 | 5.0 | 4.9 | 5.6 | 4.8 | 5.1 | 5.0 | 5.1 | 4.9 | 5.0 | 4.9 | 5.0 |
| O | 6.2 | 5.6 | 4.7 | 4.6 | 4.3 | 4.6 | 5.3 | 4.6 | 4.6 | 4.9 | 5.0 | 5.2 | 5.2 |
| P | 38.4 | 8.6 | 9.5 | 8.1 | 10.0 | 7.0 | 6.3 | 7.9 | 6.9 | 6.7 | 5.9 | 6.6 | 10.9 |

FIG. 2B

|   | 14 | 15 | 16 | 17 | 18 | 19 | 20 | 21 | 22 | 23 | 24 |
|---|---|---|---|---|---|---|---|---|---|---|---|
| A | 6.0 | 7.3 | 5.8 | 5.9 | 6.3 | 6.0 | 5.8 | 6.3 | 7.1 | 8.0 | 13.4 |
| B | 5.7 | 5.5 | 5.5 | 5.4 | 5.4 | 5.4 | 5.9 | 8.2 | 9.3 | 10.2 | 17.0 |
| C | 5.1 | 5.3 | 5.2 | 4.9 | 5.0 | 6.0 | 5.0 | 4.7 | 4.8 | 5.0 | 11.4 |
| D | 5.6 | 5.3 | 5.4 | 5.6 | 5.4 | 5.8 | 5.4 | 6.7 | 7.9 | 8.6 | 12.5 |
| E | 4.7 | 4.7 | 23.7 | 4.7 | 5.0 | 5.0 | 4.6 | 4.6 | 5.3 | 4.6 | 11.8 |
| F | 5.4 | 5.3 | 6.7 | 5.2 | 5.4 | 5.5 | 5.1 | 6.6 | 7.9 | 7.4 | 13.8 |
| G | 5.3 | 5.6 | 5.6 | 5.7 | 5.7 | 7.3 | 5.6 | 5.3 | 5.5 | 5.6 | 10.8 |
| H | 6.2 | 5.9 | 5.7 | 5.9 | 5.9 | 6.0 | 6.4 | 8.2 | 11.1 | 13.1 | 14.8 |
| I | 5.3 | 5.0 | 5.0 | 5.2 | 5.2 | 5.7 | 5.4 | 9.1 | 5.3 | 7.1 | 8.6 |
| J | 6.0 | 5.0 | 5.3 | 5.1 | 15.9 | 6.2 | 5.3 | 5.1 | 6.2 | 10.3 | 12.1 |
| K | 5.2 | 5.0 | 5.5 | 5.3 | 5.0 | 5.1 | 4.9 | 4.7 | 5.7 | 9.3 | 12.1 |
| L | 5.3 | 5.2 | 5.0 | 5.2 | 5.0 | 5.8 | 5.1 | 5.7 | 8.2 | 12.8 | 17.3 |
| M | 7.4 | 4.9 | 4.7 | 4.7 | 16.7 | 4.9 | 4.7 | 4.7 | 6.4 | 17.8 | 18.3 |
| N | 5.1 | 5.2 | 5.2 | 5.7 | 6.1 | 6.5 | 5.5 | 6.0 | 8.8 | 24.1 | 18.2 |
| O | 5.3 | 5.6 | 5.6 | 7.0 | 8.0 | 6.7 | 5.7 | 5.8 | 16.2 | 25.4 | 25.5 |
| P | 8.3 | 6.9 | 10.3 | 8.4 | 11.8 | 11.0 | 8.4 | 10.8 | 22.1 | 100.0 | 31.0 |

FIG. 2B (cont'd)

PLATE 1

| | 1 | 2 | 3 | 4 | 5 | 6 | 7 | 8 | 9 | 10 | 11 | 12 |
|---|---|---|---|---|---|---|---|---|---|---|---|---|
| A | 81.8 | 6.7 | 7.4 | 5.8 | 5.6 | 8.6 | 7.6 | 7.3 | 5.9 | 6.0 | 6.3 | 8.0 |
| B | 3.9 | 4.2 | 4.3 | 4.6 | 4.5 | 5.2 | 5.2 | 5.3 | 4.9 | 6.0 | 4.7 | 5.0 |
| C | 4.0 | 4.3 | 4.4 | 4.6 | 8.5 | 6.3 | 5.2 | 4.7 | 4.7 | 5.0 | 4.6 | 4.6 |
| D | 4.5 | 4.2 | 4.6 | 4.4 | 4.6 | 5.4 | 5.6 | 5.6 | 5.7 | 7.3 | 5.3 | 5.6 |
| E | 4.0 | 6.6 | 4.5 | 4.9 | 4.5 | 4.7 | 5.0 | 5.0 | 5.2 | 5.7 | 9.1 | 7.1 |
| F | 4.0 | 4.2 | 4.3 | 5.7 | 4.2 | 4.6 | 4.9 | 5.0 | 5.3 | 5.1 | 4.7 | 9.3 |
| G | 4.9 | 5.2 | 4.0 | 4.6 | 4.4 | 4.6 | 5.9 | 4.9 | 4.7 | 4.9 | 4.7 | 17.8 |
| H | 6.2 | 4.7 | 4.3 | 5.3 | 4.6 | 5.0 | 5.2 | 5.6 | 7.0 | 6.7 | 5.8 | 25.4 |

FIG. 3A

Plate 2

| | 1 | 2 | 3 | 4 | 5 | 6 | 7 | 8 | 9 | 10 | 11 | 12 |
|---|---|---|---|---|---|---|---|---|---|---|---|---|
| A | 7.9 | 8.3 | 5.9 | 8.6 | 5.7 | 6.2 | 6.0 | 5.8 | 6.3 | 5.8 | 7.1 | 13.4 |
| B | 4.2 | 4.5 | 4.5 | 6.6 | 13.1 | 5.2 | 5.1 | 5.2 | 5.0 | 5.0 | 4.8 | 11.4 |
| C | 4.7 | 4.3 | 4.3 | 4.9 | 4.3 | 5.5 | 4.7 | 23.7 | 5.0 | 4.6 | 5.3 | 11.8 |
| D | 4.2 | 5.3 | 4.3 | 6.9 | 5.3 | 5.4 | 5.3 | 5.6 | 5.7 | 5.6 | 5.5 | 10.8 |
| E | 4.7 | 4.5 | 4.3 | 5.2 | 5.2 | 5.0 | 5.3 | 5.0 | 5.2 | 5.4 | 5.3 | 8.6 |
| F | 4.2 | 4.1 | 4.0 | 4.6 | 4.6 | 4.8 | 5.2 | 5.5 | 5.0 | 4.9 | 5.7 | 12.1 |
| G | 5.4 | 16.9 | 4.2 | 5.2 | 4.2 | 4.9 | 7.4 | 4.7 | 16.7 | 4.7 | 6.4 | 18.3 |
| H | 5.6 | 4.6 | 4.6 | 4.6 | 4.9 | 5.2 | 5.3 | 5.6 | 8.0 | 5.7 | 16.2 | 25.5 |

FIG. 3B

PLATE 3

| | 1 | 2 | 3 | 4 | 5 | 6 | 7 | 8 | 9 | 10 | 11 | 12 |
|---|---|---|---|---|---|---|---|---|---|---|---|---|
| A | 9.9 | 5.4 | 5.4 | 6.8 | 5.9 | 5.6 | 5.7 | 5.5 | 5.4 | 5.4 | 8.2 | 10.2 |
| B | 8.1 | 5.0 | 6.3 | 5.4 | 5.1 | 5.2 | 5.6 | 5.3 | 5.6 | 5.8 | 6.7 | 8.6 |
| C | 6.7 | 5.0 | 4.8 | 5.2 | 5.0 | 5.2 | 5.2 | 5.3 | 5.2 | 5.5 | 6.6 | 7.4 |
| D | 7.9 | 5.6 | 5.6 | 5.9 | 5.7 | 5.7 | 5.7 | 5.9 | 5.9 | 6.0 | 8.2 | 13.1 |
| E | 6.7 | 5.0 | 4.7 | 4.9 | 5.2 | 4.9 | 5.2 | 5.0 | 5.1 | 6.2 | 5.1 | 10.3 |
| F | 7.0 | 5.7 | 5.0 | 6.0 | 5.4 | 5.6 | 5.2 | 5.2 | 5.2 | 5.8 | 5.7 | 12.8 |
| G | 10.4 | 5.0 | 5.6 | 5.1 | 5.1 | 5.0 | 5.0 | 5.2 | 5.7 | 6.5 | 6.0 | 24.1 |
| H | 38.4 | 9.5 | 10.0 | 6.3 | 6.9 | 5.9 | 10.9 | 6.9 | 8.4 | 11.0 | 10.8 | 100.0 |

FIG. 3C

Plate 4

|   | 1   | 2   | 3   | 4   | 5   | 6   | 7   | 8   | 9   | 10  | 11   | 12   |
|---|-----|-----|-----|-----|-----|-----|-----|-----|-----|-----|------|------|
| A | 7.4 | 5.3 | 5.6 | 6.0 | 5.9 | 6.0 | 5.7 | 5.5 | 5.4 | 5.9 | 9.3  | 17.0 |
| B | 5.2 | 5.3 | 5.5 | 5.7 | 5.4 | 5.4 | 5.6 | 5.4 | 5.4 | 5.4 | 7.9  | 12.5 |
| C | 5.4 | 5.0 | 5.6 | 5.3 | 4.9 | 7.2 | 5.4 | 6.7 | 5.4 | 5.1 | 7.9  | 13.8 |
| D | 6.1 | 5.6 | 5.7 | 6.4 | 5.7 | 6.2 | 6.2 | 5.7 | 5.9 | 6.4 | 11.1 | 14.8 |
| E | 5.1 | 5.6 | 4.9 | 5.3 | 5.3 | 5.0 | 6.0 | 5.3 | 15.9 | 5.3 | 6.2 | 12.1 |
| F | 5.2 | 5.3 | 4.9 | 5.6 | 6.0 | 5.3 | 5.3 | 5.0 | 5.0 | 5.1 | 8.2  | 17.3 |
| G | 5.3 | 4.9 | 4.8 | 5.0 | 4.9 | 4.9 | 5.1 | 5.2 | 6.1 | 5.5 | 8.8  | 18.2 |
| H | 8.6 | 8.1 | 7.0 | 7.9 | 6.7 | 6.6 | 8.3 | 10.3 | 11.8 | 8.4 | 22.1 | 31.0 |

FIG. 3D

|   | 1 | 2 | 3 | 4 | 5 | 6 | 7 | 8 | 9 | 10 | 11 | 12 | 13 |
|---|---|---|---|---|---|---|---|---|---|---|---|---|---|
| A | 0.206 | 1.557 | 0.175 | 0.124 | 0.159 | 0.135 | 0.156 | 0.1 | 0.117 | 0.125 | 0.13 | 0.321 | 0.09 |
| B | 0.156 | 0.082 | 0.073 | 0.071 | 0.073 | 0.078 | 0.074 | 0.076 | 0.073 | 0.08 | 0.081 | 0.082 | 0.087 |
| C | 0.104 | 0.065 | 0.063 | 0.063 | 0.061 | 0.066 | 0.072 | 0.08 | 0.067 | 0.061 | 0.07 | 0.066 | 0.073 |
| D | 0.11 | 0.08 | 0.067 | 0.074 | 0.07 | 0.073 | 0.077 | 0.077 | 0.073 | 0.071 | 0.072 | 0.069 | 0.076 |
| E | 0.076 | 0.066 | 0.062 | 0.06 | 0.076 | 0.066 | 0.072 | 0.061 | 0.061 | 0.065 | 0.08 | 0.064 | 0.07 |
| F | 0.099 | 0.072 | 0.067 | 0.068 | 0.066 | 0.07 | 0.111 | 0.066 | 0.077 | 0.071 | 0.072 | 0.082 | 0.185 |
| G | 0.084 | 0.077 | 0.063 | 0.064 | 0.06 | 0.062 | 0.067 | 0.066 | 0.063 | 0.061 | 0.06 | 0.072 | 0.07 |
| H | 0.078 | 0.067 | 0.064 | 0.066 | 0.063 | 0.066 | 0.076 | 0.069 | 0.076 | 0.067 | 0.071 | 0.071 | 0.211 |
| I | 0.067 | 0.062 | 0.062 | 0.101 | 0.059 | 0.061 | 0.066 | 0.069 | 0.061 | 0.064 | 0.068 | 0.06 | 0.072 |
| J | 0.081 | 0.065 | 0.064 | 0.072 | 0.076 | 0.077 | 0.077 | 0.083 | 0.073 | 0.075 | 0.08 | 0.08 | 0.088 |
| K | 0.071 | 0.061 | 0.055 | 0.059 | 0.057 | 0.068 | 0.067 | 0.067 | 0.06 | 0.057 | 0.059 | 0.063 | 0.062 |
| L | 0.083 | 0.062 | 0.059 | 0.06 | 0.061 | 0.061 | 0.067 | 0.07 | 0.062 | 0.06 | 0.068 | 0.067 | 0.067 |
| M | 0.072 | 0.158 | 0.06 | 0.059 | 0.057 | 0.062 | 0.077 | 0.09 | 0.061 | 0.059 | 0.068 | 0.068 | 0.082 |
| N | 0.084 | 0.079 | 0.068 | 0.067 | 0.063 | 0.073 | 0.076 | 0.073 | 0.064 | 0.075 | 0.073 | 0.086 | 0.079 |
| O | 0.084 | 0.065 | 0.066 | 0.066 | 0.067 | 0.061 | 0.063 | 0.067 | 0.066 | 0.078 | 0.08 | 0.084 | 0.088 |
| P | 0.111 | 0.094 | 0.086 | 0.078 | 0.076 | 0.067 | 0.091 | 0.078 | 0.075 | 0.081 | 0.085 | 0.095 | 0.091 |

FIG. 4A

|   | 14 | 15 | 16 | 17 | 18 | 19 | 20 | 21 | 22 | 23 | 24 | Max Value |
|---|---|---|---|---|---|---|---|---|---|---|---|---|
| A | 0.111 | 0.131 | 0.111 | 0.145 | 0.11 | 0.109 | 0.117 | 0.109 | 0.1 | 0.165 | 0.098 | 1.631 |
| B | 0.082 | 0.096 | 0.08 | 0.081 | 0.092 | 0.093 | 0.086 | 0.105 | 0.12 | 0.111 | 0.114 | |
| C | 0.081 | 0.081 | 0.069 | 0.075 | 0.076 | 0.098 | 0.081 | 0.085 | 0.062 | 0.083 | 0.062 | |
| D | 0.078 | 0.08 | 0.102 | 0.095 | 0.084 | 0.116 | 0.126 | 0.136 | 0.14 | 0.13 | 0.131 | |
| E | 0.064 | 0.075 | 0.082 | 0.085 | 0.097 | 0.108 | 0.107 | 0.099 | 0.082 | 0.083 | 0.085 | |
| F | 0.078 | 0.09 | 0.1 | 0.111 | 0.112 | 0.106 | 0.14 | 0.141 | 0.149 | 0.131 | 0.144 | |
| G | 0.076 | 0.079 | 0.08 | 0.161 | 0.082 | 0.093 | 0.089 | 0.086 | 0.09 | 0.087 | 0.088 | |
| H | 0.079 | 0.084 | 0.087 | 0.093 | 0.094 | 0.094 | 0.104 | 0.116 | 0.107 | 0.12 | 0.068 | |
| I | 0.117 | 0.091 | 0.085 | 0.073 | 0.084 | 0.092 | 0.081 | 0.092 | 0.088 | 0.09 | 0.063 | |
| J | 0.099 | 0.105 | 0.106 | 0.096 | 0.099 | 0.124 | 0.124 | 0.141 | 0.164 | 0.165 | 0.153 | |
| K | 0.073 | 0.097 | 0.066 | 0.063 | 0.066 | 0.105 | 0.098 | 0.083 | 0.102 | 0.091 | 0.086 | |
| L | 0.073 | 0.107 | 0.133 | 0.07 | 0.08 | 0.121 | 0.11 | 0.131 | 0.148 | 0.137 | 0.12 | |
| M | 0.072 | 0.072 | 0.128 | 0.063 | 0.084 | 0.081 | 0.078 | 0.094 | 0.091 | 0.111 | 0.111 | |
| N | 0.078 | 0.083 | 0.079 | 0.136 | 1.631 | 0.135 | 0.096 | 0.108 | 0.127 | 0.176 | 0.134 | |
| O | 0.072 | 0.077 | 0.078 | 0.085 | 0.091 | 0.093 | 0.08 | 0.077 | 0.076 | 0.077 | 0.1 | |
| P | 0.1 | 0.094 | 0.092 | 0.106 | 0.152 | 0.102 | 0.091 | 0.116 | 0.112 | 0.122 | 0.113 | |

FIG. 4A (cont'd)

|   | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| A | 12.6 | 95.5 | 10.7 | 7.6 | 9.7 | 8.3 | 9.6 | 6.1 | 7.2 | 7.7 | 8.0 | 19.7 | 5.5 | 6.8 | 8.0 | 6.8 | 8.9 | 6.7 | 6.7 | 7.2 | 6.7 | 6.1 | 10.1 | 6.0 |
| B | 9.6 | 5.0 | 4.5 | 4.4 | 4.5 | 4.8 | 4.5 | 4.7 | 4.5 | 4.9 | 5.0 | 5.0 | 5.3 | 5.0 | 5.9 | 4.9 | 5.0 | 5.6 | 5.7 | 5.3 | 6.4 | 7.4 | 6.8 | 7.0 |
| C | 6.4 | 4.0 | 3.9 | 3.9 | 3.7 | 4.0 | 4.4 | 4.9 | 4.1 | 3.7 | 4.3 | 4.0 | 4.5 | 5.0 | 5.0 | 4.2 | 4.6 | 4.7 | 6.0 | 5.0 | 5.2 | 3.8 | 5.1 | 3.8 |
| D | 6.7 | 4.9 | 4.1 | 4.5 | 4.3 | 4.5 | 4.7 | 4.7 | 4.5 | 4.4 | 4.4 | 4.2 | 4.7 | 4.8 | 4.9 | 6.3 | 5.8 | 5.2 | 7.1 | 7.7 | 8.3 | 8.6 | 8.0 | 8.0 |
| E | 4.7 | 4.0 | 3.8 | 3.7 | 4.7 | 4.0 | 4.4 | 3.7 | 3.7 | 4.0 | 4.9 | 3.9 | 4.3 | 3.9 | 4.6 | 5.0 | 5.2 | 5.9 | 6.6 | 6.6 | 6.1 | 5.0 | 5.1 | 5.2 |
| F | 6.1 | 4.4 | 4.1 | 4.2 | 4.0 | 4.3 | 6.8 | 4.0 | 4.7 | 4.4 | 4.4 | 5.0 | 11.3 | 4.8 | 5.5 | 6.1 | 6.8 | 6.9 | 6.5 | 8.6 | 8.6 | 9.1 | 8.0 | 8.8 |
| G | 5.2 | 4.7 | 3.9 | 3.9 | 3.7 | 3.8 | 4.1 | 4.0 | 3.9 | 3.7 | 3.7 | 4.4 | 4.3 | 4.7 | 4.8 | 4.9 | 9.9 | 5.0 | 5.7 | 5.5 | 5.3 | 5.5 | 5.3 | 5.4 |
| H | 4.8 | 4.1 | 3.9 | 4.0 | 3.9 | 4.0 | 4.7 | 4.2 | 4.7 | 4.1 | 4.4 | 4.4 | 12.9 | 4.8 | 5.2 | 5.3 | 5.7 | 5.8 | 5.8 | 6.4 | 7.1 | 6.6 | 7.4 | 4.2 |
| I | 4.1 | 3.8 | 3.8 | 6.2 | 3.6 | 3.7 | 4.0 | 4.2 | 3.7 | 3.9 | 4.2 | 3.7 | 4.4 | 7.2 | 5.6 | 5.2 | 4.5 | 5.2 | 5.6 | 5.0 | 5.6 | 5.4 | 5.5 | 3.9 |
| J | 5.0 | 4.0 | 3.9 | 4.4 | 4.7 | 4.7 | 4.7 | 5.1 | 4.5 | 4.6 | 4.9 | 4.9 | 5.4 | 6.1 | 6.4 | 6.5 | 5.9 | 6.1 | 7.6 | 7.6 | 8.6 | 10.1 | 10.1 | 9.4 |
| K | 4.4 | 3.7 | 3.4 | 3.6 | 3.5 | 4.2 | 4.1 | 4.1 | 3.7 | 3.5 | 3.6 | 3.9 | 3.8 | 4.5 | 5.9 | 4.0 | 3.9 | 4.0 | 6.4 | 6.0 | 5.1 | 6.3 | 5.6 | 5.3 |
| L | 5.1 | 3.8 | 3.6 | 3.7 | 3.7 | 3.7 | 4.1 | 4.3 | 3.8 | 3.7 | 4.2 | 4.1 | 4.1 | 4.5 | 6.6 | 8.2 | 4.3 | 4.9 | 7.4 | 6.7 | 8.0 | 9.1 | 8.4 | 7.4 |
| M | 4.4 | 9.7 | 3.7 | 3.6 | 3.5 | 3.8 | 4.7 | 5.5 | 3.7 | 3.6 | 4.2 | 4.2 | 5.0 | 4.4 | 4.4 | 7.8 | 3.9 | 5.2 | 5.0 | 4.8 | 5.8 | 5.6 | 6.8 | 6.8 |
| N | 5.2 | 4.8 | 4.2 | 4.1 | 3.9 | 4.5 | 4.7 | 4.5 | 3.9 | 4.6 | 4.5 | 5.3 | 4.8 | 4.8 | 5.1 | 4.8 | 8.3 | 100.0 | 8.3 | 5.9 | 6.6 | 7.8 | 10.8 | 8.2 |
| O | 5.2 | 4.0 | 4.0 | 4.0 | 4.1 | 3.7 | 3.9 | 4.1 | 4.0 | 4.8 | 4.9 | 5.2 | 5.4 | 4.4 | 4.7 | 4.8 | 5.2 | 5.6 | 5.7 | 4.9 | 4.7 | 4.7 | 4.7 | 6.1 |
| P | 6.8 | 5.8 | 5.3 | 4.8 | 4.7 | 4.1 | 5.6 | 4.8 | 4.6 | 5.0 | 5.2 | 5.8 | 5.6 | 6.1 | 5.8 | 5.6 | 6.5 | 9.3 | 6.3 | 5.6 | 7.1 | 6.9 | 7.5 | 6.9 |

FIG. 4B

PLATE 5

| | 1 | 2 | 3 | 4 | 5 | 6 | 7 | 8 | 9 | 10 | 11 | 12 |
|---|---|---|---|---|---|---|---|---|---|---|---|---|
| A | 12.63 | 10.73 | 9.75 | 9.56 | 7.17 | 7.97 | 5.52 | 8.03 | 8.89 | 6.68 | 6.68 | 10.12 |
| B | 6.38 | 3.86 | 3.74 | 4.41 | 4.11 | 4.29 | 4.48 | 4.97 | 4.60 | 6.01 | 5.21 | 5.09 |
| C | 4.66 | 3.80 | 4.66 | 4.41 | 3.74 | 4.90 | 4.29 | 4.60 | 5.21 | 6.62 | 6.07 | 5.09 |
| D | 5.15 | 3.86 | 3.68 | 4.11 | 3.86 | 3.68 | 4.29 | 4.84 | 9.87 | 5.70 | 5.27 | 5.33 |
| E | 4.11 | 3.80 | 3.62 | 4.05 | 3.74 | 4.17 | 4.41 | 5.58 | 4.48 | 5.64 | 5.64 | 5.52 |
| F | 4.35 | 3.37 | 3.49 | 4.11 | 3.68 | 3.62 | 3.80 | 5.95 | 3.86 | 6.44 | 5.09 | 5.58 |
| G | 4.41 | 3.68 | 3.49 | 4.72 | 3.74 | 4.17 | 5.03 | 4.41 | 3.86 | 4.97 | 5.76 | 6.81 |
| H | 5.15 | 4.05 | 4.11 | 3.86 | 4.05 | 4.90 | 5.40 | 4.72 | 5.21 | 5.70 | 4.72 | 4.72 |

FIG. 5A

Plate 6

| | 1 | 2 | 3 | 4 | 5 | 6 | 7 | 8 | 9 | 10 | 11 | 12 |
|---|---|---|---|---|---|---|---|---|---|---|---|---|
| A | 95.46 | 7.60 | 8.28 | 6.13 | 7.66 | 19.68 | 6.81 | 6.81 | 6.74 | 7.17 | 6.13 | 6.01 |
| B | 3.99 | 3.86 | 4.05 | 4.90 | 3.74 | 4.05 | 4.97 | 4.23 | 4.66 | 4.97 | 3.80 | 3.80 |
| C | 4.05 | 3.68 | 4.05 | 3.74 | 3.99 | 3.92 | 3.92 | 5.03 | 5.95 | 6.56 | 5.03 | 5.21 |
| D | 4.72 | 3.92 | 3.80 | 4.05 | 3.74 | 4.41 | 4.66 | 4.90 | 5.03 | 5.46 | 5.52 | 5.40 |
| E | 3.80 | 6.19 | 3.74 | 4.23 | 3.92 | 3.68 | 7.17 | 5.21 | 5.15 | 4.97 | 5.40 | 3.86 |
| F | 3.74 | 3.62 | 4.17 | 4.11 | 3.49 | 3.86 | 4.48 | 4.05 | 4.05 | 6.01 | 6.25 | 5.27 |
| G | 9.69 | 3.62 | 3.80 | 5.52 | 3.62 | 4.17 | 4.41 | 7.85 | 5.15 | 4.78 | 5.58 | 6.81 |
| H | 3.99 | 4.05 | 3.74 | 4.11 | 4.78 | 5.15 | 4.41 | 4.78 | 5.58 | 4.90 | 4.66 | 6.13 |

FIG. 5B

PLATE 7

| | 1 | 2 | 3 | 4 | 5 | 6 | 7 | 8 | 9 | 10 | 11 | 12 |
|---|---|---|---|---|---|---|---|---|---|---|---|---|
| A | 9.56 | 4.48 | 4.48 | 4.54 | 4.48 | 4.97 | 5.33 | 5.89 | 4.97 | 5.70 | 6.44 | 6.81 |
| B | 6.74 | 4.11 | 4.29 | 4.72 | 4.48 | 4.41 | 4.66 | 4.90 | 5.82 | 7.11 | 8.34 | 7.97 |
| C | 6.07 | 4.11 | 4.05 | 6.81 | 4.72 | 4.41 | 11.34 | 5.52 | 6.81 | 6.50 | 8.65 | 8.03 |
| D | 4.78 | 3.92 | 3.86 | 4.66 | 4.66 | 4.35 | 12.94 | 5.15 | 5.70 | 5.76 | 7.11 | 7.36 |
| E | 4.97 | 3.92 | 4.66 | 4.72 | 4.48 | 4.90 | 5.40 | 6.44 | 5.89 | 7.60 | 8.65 | 10.12 |
| F | 5.09 | 3.62 | 3.74 | 4.11 | 3.80 | 4.17 | 4.11 | 6.56 | 4.29 | 7.42 | 8.03 | 8.40 |
| G | 5.15 | 4.17 | 3.86 | 4.66 | 3.92 | 4.48 | 4.84 | 5.09 | 8.34 | 8.28 | 6.62 | 10.79 |
| H | 6.81 | 5.27 | 4.66 | 5.58 | 4.60 | 5.21 | 5.58 | 5.76 | 6.50 | 6.25 | 7.11 | 7.48 |

FIG. 5C

Plate 8

| | 1 | 2 | 3 | 4 | 5 | 6 | 7 | 8 | 9 | 10 | 11 | 12 |
|---|---|---|---|---|---|---|---|---|---|---|---|---|
| A | 5.03 | 4.35 | 4.78 | 4.66 | 4.90 | 5.03 | 5.03 | 4.90 | 5.64 | 5.27 | 7.36 | 6.99 |
| B | 4.90 | 4.54 | 4.48 | 4.72 | 4.35 | 4.23 | 4.78 | 6.25 | 5.15 | 7.73 | 8.58 | 8.03 |
| C | 4.41 | 4.17 | 4.29 | 4.05 | 4.35 | 5.03 | 4.78 | 6.13 | 6.87 | 8.58 | 9.14 | 8.83 |
| D | 4.11 | 4.05 | 4.05 | 4.23 | 4.11 | 4.35 | 4.84 | 5.33 | 5.76 | 6.38 | 6.56 | 4.17 |
| E | 3.99 | 4.41 | 4.72 | 5.09 | 4.60 | 4.90 | 6.07 | 6.50 | 6.07 | 7.60 | 10.06 | 9.38 |
| F | 3.80 | 3.68 | 3.74 | 4.29 | 3.68 | 4.11 | 4.48 | 8.15 | 4.90 | 6.74 | 9.07 | 7.36 |
| G | 4.84 | 4.11 | 4.48 | 4.48 | 4.60 | 5.27 | 4.78 | 4.84 | 100.00 | 5.89 | 7.79 | 8.22 |
| H | 5.76 | 4.78 | 4.11 | 4.78 | 4.97 | 5.82 | 6.13 | 5.64 | 9.32 | 5.58 | 6.87 | 6.93 |

| Clone | Fusion | Immunogen | ELISA 110905 GST-CD63 | ELISA 110905 GST-CO | ELISA 110909 GST-CD63 | ELISA 110909 GST-CO | Subcloning SC1 | ELISA GST-CD63 | ELISA GST-CO | Subcloning SC2 | ELISA 111005 GST-CD63 | ELISA 111005 GST-CO | Frozen | Frozen | DESIGNATION | |
|---|---|---|---|---|---|---|---|---|---|---|---|---|---|---|---|---|
| 58.3H12 | FX58 | fixed LoVo Cells | POS | NEG | 1.203 | 0.148 | 9/9/11 | | | | | | | | | |
| 58.5B6 | FX58 | fixed LoVo Cells | NEG | POS | 0.192 | 0.963 | 9/9/11 | | | | | | | | | |
| 58.8G9 | FX58 | fixed LoVo Cells | POS | NEG | 0.991 | 0.181 | 9/9/11 | | | | | | | | | |
| 58.3H12.B7 | FX58 | fixed LoVo Cells | | | | | | POS | NEG | 10/1/11 | | | | | | |
| 58.3H12.D5 | FX58 | fixed LoVo Cells | | | | | | POS | NEG | 10/1/11 | | | | | | |
| 58.3H12.F5 | FX58 | fixed LoVo Cells | | | | | | POS | NEG | 10/1/11 | | | | | | |
| 58.5B6.C7 | FX58 | fixed LoVo Cells | | | | | | NEG | POS | 10/1/11 | | | | | | |
| 58.5B6.E6 | FX58 | fixed LoVo Cells | | | | | | NEG | POS | 10/1/11 | | | | | | |
| 58.5B6.G5 | FX58 | fixed LoVo Cells | | | | | | NEG | POS | 10/1/11 | | | | | | |
| 58.3H12.B7.B9 | FX58 | fixed LoVo Cells | | | | | | | | | POS | NEG | 10/13/11 | | | |
| 58.3H12.B7.D8 | FX58 | fixed LoVo Cells | | | | | | | | | POS | NEG | 10/13/11 | | | |
| 58.3H12.D5.B11 | FX58 | fixed LoVo Cells | | | | | | | | | POS | NEG | 10/13/11 | | | |
| 58.3H12.D5.F10 | FX58 | fixed LoVo Cells | | | | | | | | | POS | NEG | 10/13/11 | 10/17/11 | Z63.5 | Anti-CD6 |
| 58.3H12.C8 | FX58 | fixed LoVo Cells | | | | | | | | | POS | NEG | 10/13/11 | | | |
| 58.3H12.C10 | FX58 | fixed LoVo Cells | | | | | | | | | POS | NEG | 10/13/11 | | | |
| 58.5B6.C7.C12 | FX58 | fixed LoVo Cells | | | | | | | | | NEG | POS | 10/13/11 | | | |
| 58.5B6.C7.D10 | FX58 | fixed LoVo Cells | | | | | | | | | NEG | POS | 10/13/11 | | | |
| 58.5B6.E6.E9 | FX58 | fixed LoVo Cells | | | | | | | | | NEG | POS | 10/13/11 | | | |
| 58.5B6.E6.H6 | FX58 | fixed LoVo Cells | | | | | | | | | NEG | POS | 10/13/11 | | | |
| 58.5B6.G5.B10 | FX58 | fixed LoVo Cells | | | | | | | | | NEG | POS | 10/13/11 | | | |
| 58.5B6.G5.H5 | FX58 | fixed LoVo Cells | | | | | | | | | NEG | POS | 10/13/11 | 10/17/11 | AZM8.2 | Anti-TSP |

FIG. 7

HYBRIDOMA CLONES, MONOCLONAL ANTIBODIES, AND METHODS OF USE

CROSS-REFERENCE TO RELATED APPLICATIONS

The present application is the national stage of International Patent Application No. PCT/US2013/041256, filed on May 15, 2013, the entire contents and disclosure of which are herein incorporated by reference.

FIELD OF THE INVENTION

This invention relates to hybridoma clones and monoclonal antibodies, and more particularly, hybridoma clone and monoclonal antibodies directed to a human CD63 protein, and methods of use.

BACKGROUND OF THE INVENTION

The human CD63 antigen has a diverse distribution on the surface and in the cytoplasm of many cell types including lymphoid, myeloid, endothelial cells and melanoma. CD63 is intracellular lysosomal/endosomal/granule protein that is translocated to cell surface upon activation of platelets, endothelial cells, and granulocytes (activation marker). CD63 is also expressed on monocytes/macrophages and endothelium.

There are several anti-CD63 monoclonal antibodies described in the literature, however, a need exists for new anti-CD63 antibodies having unique genetic and amino acid structures, including unique binding and functional characteristics. The development of new anti-CD63 monoclonal antibodies and hybridoma cells lines that produce such monoclonal antibodies would be a valuable tool for functional studies of newly discovered tetraspanins including, for example, for use in more effectively treating a variety of cancers and purification of exosomes.

SUMMARY OF THE INVENTION

The present invention is directed to antibodies and fragments thereof that bind to human CD63. The antibodies may be labeled with one or more labels selected from the group consisting of a biotin label, a fluorescent label, an enzyme label, a coenzyme label, a chemiluminescent label, and a radioactive isotope label.

The invention is also directed to a hybridoma cell line that produces the antibody, and to methods of treating cancer and purifying exosomes using the antibody or antigen-binding fragments thereof.

The present invention is also directed to a method for diagnosing cancer, wherein the method comprises: reacting an anti-CD63 antibody with a sample collected from the subject; detecting an CD63 protein in the sample; and diagnosing cancer when the level of CD63 protein is higher in the sample than in a normal sample, wherein the sample collected from the subject is at least one sample selected from the group consisting of a tissue sample, a blood sample, a serum sample, and a plasma sample.

The antibodies of the present invention are preferably isolated monoclonal antibodies having specific binding properties against a human CD63 protein, more preferably against human CD63 in its native form.

The invention is further directed to pharmaceutical compositions comprising an antibody of the invention and a pharmaceutically acceptable carrier.

The invention is also directed to an anti-CD63 monoclonal antibody for use in treatment of cancer. In some aspects, the invention is directed to use of an anti-CD63 monoclonal antibody for the manufacture of a medicament for use in treatment of cancer. In other aspects, the invention is directed to use of an anti-CD63 monoclonal antibody in the preparation of a kit for diagnosing cancer. The cancer to be treated or diagnosed may be, for example, breast cancer, pancreatic cancer, prostate cancer, melanoma, colon cancer, lung cancer, and thyroid cancer.

BRIEF DESCRIPTION OF THE DRAWINGS

Illustrative and exemplary embodiments of the invention are shown in the drawings in which:

FIGS. 2A and 2B show the raw data for plates 1-4 from the initial hybridoma ELISA screening using binding GST-CD63. Overall, supernatant from the wells were screened for binding to GST-CD63.

FIGS. 3A-3D show the data from the 384 well ELISA plates corresponding to plates 1-4 of the eight 96-well hybridoma plates. Highlighted wells from the 96-well plate show selected wells for expansion. Positive controls were put in well A1 of the 384-well screening plate.

FIGS. 4A and 4B show the raw data for plates 5-8 from the initial hybridoma ELISA screening using binding GST-CD63. Overall, supernatant from the wells were screened for binding to GST-CD63.

FIGS. 5A-5D show the data from the 384 well ELISA plates corresponding to plates 5-8 of the eight 96-well hybridoma plates. Highlighted wells from the 96-well plate show selected wells for expansion. A positive control was put in well A2 of the 384-well screening plate.

FIG. 7 shows a summary of the overall development of the final hybridoma clones including response in screening assays for the parental, daughter and granddaughter clones from the limiting dilutions experiments. Final clones have a fusion identification ID and a designation name as shown.

DETAILED DESCRIPTION OF THE INVENTION

Figure 1:
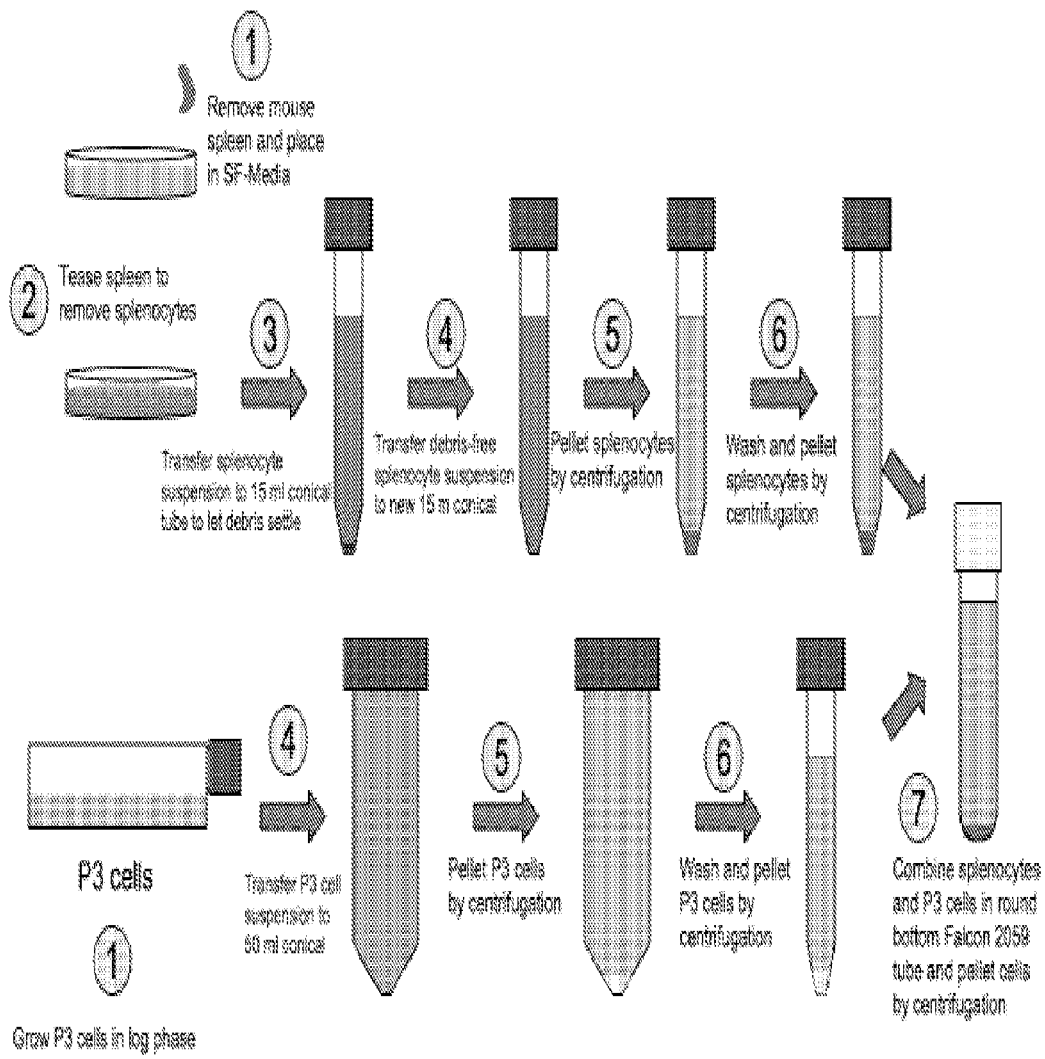
FIG. 1 Illustrates and shows the steps taken to produce hybridomas disclosed herein.

The present invention is directed to an antibody that recognizes human CD63. The invention is also directed to a hybridoma cell line that produces the antibody, and to methods of treating cancer and purifying exosomes using the antibody. More specifically, the invention includes a murine hybridoma clone, designated as Z63.5 and having ATCC accession number PTA-120178, that secretes a murine monoclonal antibody to the human CD63 protein. The anti-CD63 antibody Z63.5 recognizes human CD63 in its native form, which is expressed on lysosome membranes and the cellular membrane. The antibody produced by Z63.5 is of a murine IgG1, kappa chain isotype.

The term "antibody" is used herein in the broadest sense and refers generally to a molecule that contains at least one antigen binding site that immunospecifically binds to a particular antigen target of interest. The term "antibody" thus includes but is not limited to antibodies and variants thereof, fragments of antibodies and variants thereof, peptibodies and variants thereof, and antibody mimetics that mimic the structure and/or function of an antibody or a specified fragment or portion thereof, including single chain antibodies and fragments thereof. The term "antibody," thus includes full-length antibodies and/or their variants as well as fragments thereof. Binding of an antibody to a target can cause a variety of effects, such as but not limited to, it modulates, decreases, increases, antagonizes, agonizes, mitigates, alleviates, blocks, inhibits, abrogates and/or interferes with at least one target activity or binding, or with receptor activity or binding, in vitro, in situ, and/or in vivo.

The present invention, thus, encompasses antibodies capable of binding to a biological molecule (such as an antigen or receptor) or portions thereof, including but not limited to Fab, Fab' and F(ab')$_2$, facb, pFc', Fd, Fv or scFv fragments. (See, e.g., CURRENT PROTOCOLS IN IMMUNOLOGY, Colligan et al., eds., John Wiley & Sons, Inc., NY, 1994-2001); diabodies; linear antibodies (Zapata et al., (1995) Protein Eng. 8(10):1057); single-chain antibody molecules; and multispecific antibodies formed from antibody fragments.

Accordingly, antibody is used in the broadest sense and specifically covers, for example, single anti-CD63 monoclonal antibodies (including agonist, antagonist, and neutralizing antibodies), anti-CD63 antibody compositions with polyepitopic specificity, single chain anti-CD63 antibodies, and fragments of anti-CD63 antibodies. The term "monoclonal antibody" as used herein refers to an antibody obtained from a population of substantially homogeneous antibodies, i.e., the individual antibodies comprising the population are identical except for possible naturally occurring mutations that may be present in minor amounts.

Specific antibody fragments of the present invention include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883), (viii) bispecific single chain Fv (WO 03/11161) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448). The antibody fragments may be modified. For example, the molecules may be stabilized by the incorporation of disulfide bridges linking the VH and VL domains (Reiter et al., 1996, Nature Biotech. 14:1239-1245).

"Fv" is the minimum antibody fragment that contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the VH and VL domains of antibody, wherein these domains are present in a single polypeptide chain. Preferably, the Fv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) Proc. Natl. Acad. Sci. USA 90:6444.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

A "native sequence CD63 polypeptide" comprises a polypeptide having the same amino acid sequence as the corresponding CD63 polypeptide derived from nature. Such native sequence CD63 polypeptides can be isolated from nature or can be produced by recombinant or synthetic means. The term "native sequence CD63 polypeptide" specifically encompasses naturally occurring truncated or secreted forms of the specific CD63 polypeptide (e.g., an extracellular domain sequence), naturally-occurring variant forms (e.g., alternatively spliced forms) and naturally-occurring allelic variants of the polypeptide. In various embodiments of the invention, the native sequence CD63 polypeptides disclosed herein are mature or full-length native sequence polypeptides comprising the full-length amino acids sequences shown in the accompanying figures.

The terms "individual," "subject," and "patient," used interchangeably herein, refer to an animal, preferably a mammalian (including nonprimate and primate), including, but not limited to, murines, simians, humans, mammalian farm animals (e.g., bovine, porcine, ovine), mammalian sport animals (e.g., equine), and mammalian pets (e.g., canine and feline); preferably the term refers to humans.

As used herein, the terms "treatment", "treating", and the like, refer to obtaining a desired pharmacologic, and/or physiologic effect. The effect may be therapeutic in terms of a partial or complete cure for a disease, symptom, and/or adverse effect attributable to the disease. "Treatment," as used herein, includes administration of a compound of the present invention for treatment of a disease or condition in a mammal, particularly in a human, and includes: (a) inhibiting the disease, i.e., arresting its development; (b) providing palliative care, i.e., reducing and preventing the suffering of a patient; and (c) relieving the disease, i.e., causing regression of the disease or disorder or alleviating symptoms or complications thereof. Dosage regimens may be adjusted to provide the optimum desired response.

Monoclonal Antibodies

The anti-CD63 antibodies may, alternatively, be monoclonal antibodies. Monoclonal antibodies may be prepared using hybridoma methods, such as those described by Kohler and Milstein (1975) Nature 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

An immunizing agent typically includes the CD63 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding (1986) Monoclonal Antibodies: Principles and Practice, Academic Press, pp. 59-103). Immortalized cell lines may be transformed mammalian cells, particularly myeloma cells of rodent, bovine and human origin. Rat or mouse myeloma cell lines may be employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, J. (1984) Immunol. 133:3001; Brodeur et al. (1987) Monoclonal Antibody Production Techniques and Applications, Marcel Dekker, Inc., New York, pp. 51-631).

The culture medium in which the hybridoma cells are cultured can then be assayed for the presence of monoclonal antibodies directed against CD63. The binding specificity of monoclonal antibodies produced by the hybridoma cells can be determined by inmunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard (1980) Anal. Biochem. 107:220.

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures, e.g., by using oligonucleotide probes that are capable of binding specifically to genes encoding the heavy and light chains of murine antibodies. The hybridoma cells of the invention serve as a preferred source of such DNA. Once isolated, the DNA may be placed into expression vectors, which are then transfected into host cells, such as, simian COS cells, Chinese hamster ovary (CHO) cells, or myeloma cells that do not otherwise produce immunoglobulin protein, in order to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bifunctional or multifunctional antibody with nonidentical antigenic binding specificities, each of which may be monovalent, bivalent, or multivalent.

The antibodies of the present invention may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof can be accomplished using routine techniques known in the art.

The anti-CD63 monoclonal antibodies of the invention may be whole or an antigen-binding fragment of the antibody that binds to a CD63 polypeptide, preferably a native sequence CD63 polypeptide. Furthermore, in a preferred embodiment the monoclonal antibody is identified as lab number mAb Z63.5 having recognition of a CD63 protein from at least one colon cancer cell line, more preferably at least three.

In one non-limiting embodiment the monoclonal antibody is produced by the hybridoma cell line designated as Z63.5 and having ATCC accession number PTA-120178, which comprises the amino acid sequences, or having a conservative substitution of an amino acid thereof, wherein said antibody or functional fragment thereof binds to a CD63 protein and wherein said antibody or functional fragment thereof having a conservative substitution of an amino acid binds the same neoplastic cell or antigen thereof as said antibody or functional fragment thereof.

More specifically, the monoclonal antibody of the invention comprises a heavy chain variable region (HCVR) and a light chain variable region (LCVR), wherein said HCVR comprises: a) a peptide at CDRH1, b) a peptide at CDRH2, c) a peptide at CDRH3, and wherein said LCVR comprises: a) a peptide at CDRL1, b) a peptide at CDRL2, and c) a peptide at CDRL3.

Human and Humanized Antibodies

The murine monoclonal antibodies of the present invention can be humanized to reduce the immunogenicity for use in humans. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al. (1986) Nature 321:522; Riechmann et al. (1988) Nature 332:323; and, Presta (1992) Curr. Op. Struct. Biol. 2:593).

Methods for humanizing non-human antibodies are well known in the art. An example approach is to make mouse-human chimeric antibodies having the original variable region of the murine monoclonal antibodies, joined to constant regions of a human immunoglobulin. Chimeric antibodies and methods for their production are known in the art. See, e.g., Cabilly et al., European Patent EP0125023 (published Mar. 3, 2002); Taniguchi et al., European Patent EP0171496 (published May 26, 1993); Morrison et al., European Patent Application EP0173494 (published Jan. 18, 1986); Neuberger et al., International Publication No. WO/1986/01533, (published Mar. 13, 1986); Kudo et al., European Patent Application EP0184187 (published Jun. 11, 1986); Robinson et al., International Publication No. WO/1987/002671 (published May 7, 1987); Liu et al. (1987) Proc. Natl. Acad. Sci. USA 84:3439; Sun et al. (1987) Proc. Natl. Acad. Sci. USA 84:214; Better et al. (1988) Science 240:1041. These references are incorporated herein by reference. Generally, DNA segments encoding the H and L chain antigen-binding regions of the murine mAb can be cloned from the mAb-producing hybridoma cells, which can then be joined to DNA segments encoding $C_H$ and $C_L$ regions of a human immunoglobulin, respectively, to produce murine-human chimeric immunoglobulin-encoding genes.

A chimeric antibody can be further humanized by replacing sequences of the Fv variable region which are not directly involved in antigen binding with equivalent sequences from human Fv variable regions. General methods for generating humanized antibodies are provided by Morrison, S. L., 1985, Science 229:1202-1207 by Oi et al., 1986, BioTechniques 4:214, and by Queen et al. U.S. Pat. Nos. 5,585,089, 5,693,761 and 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPIIbIIIa antibody producing hybridoma. The recombinant DNA encoding the chimeric antibody can then be cloned into an appropriate expression vector.

Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al. (1986) Nature 321:522; Riechmann et al. (1988) Nature 332:323; Verhoeyen et al. (1988) Science 239:1534), by substituting rodent CDRs or CDR sequences for the corresponding sequences of a human antibody. See also U.S. Pat. No. 5,225,539 and Beidler et al. 1988 J. Immunol. 141:4053. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter, J. Mol. Biol., 227:381 (1991); Marks et al. J. Mol. Biol., 222:581 (1991)). The techniques of Cole et al. and Boemer et al. are also available for the preparation of human monoclonal antibodies (Cole et al., Monoclonal Antibodies and Cancer Therapy, Alan R. Liss, p. 77 (1985) and Boerner et al. J. Immunol., 147(1):86 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al. Bio/Technology 10:779 (1992); Lonberg et al. Nature 368:856 (1994); Morrison, Nature 368:812 (1994); Fishwild et al. Nature Biotechnology 14:845 (1996); Neuberger, Nature Biotechnology 14:826 (1996); Lonberg and Huszar, Intern. Rev. Immunol. 13:65 (1995).

Pharmaceutical Compositions of Antibodies

In other embodiments there is provided a pharmaceutical composition including an antibody as described above together with a pharmaceutically acceptable carrier, diluent or excipient.

In the preparation of the pharmaceutical compositions comprising the antibodies described in the teachings herein, a variety of vehicles and excipients and routes of administration may be used, as will be apparent to the skilled artisan. Representative formulation technology is taught in, inter alia, Remington: The Science and Practice of Pharmacy, 19th Ed., Mack Publishing Co., Easton, Pa. (1995) and Handbook of Pharmaceutical Excipients, 3rd Ed, Kibbe, A. H. ed., Washington D.C., American Pharmaceutical Association (2000); hereby incorporated by reference in their entirety.

The pharmaceutical compositions will generally comprise a pharmaceutically acceptable carrier and a pharmacologically effective amount of an antibody, or mixture of antibodies.

The pharmaceutical composition may be formulated as powders, granules, solutions, suspensions, aerosols, solids, pills, tablets, capsules, gels, topical creams, suppositories, transdermal patches, and other formulations known in the art.

For the purposes described herein, pharmaceutically acceptable salts of the antibodies is intended to include any art recognized pharmaceutically acceptable salts, including for example, organic and inorganic acids and/or bases. Examples of salts include sodium, potassium, lithium, ammonium, calcium, as well as primary, secondary, and tertiary amines, esters of lower hydrocarbons, such as methyl, ethyl, and propyl. Other salts include organic acids, such as acetic acid, propionic acid, pyruvic acid, maleic acid, succinic acid, tartaric acid, citric acid, benzoic acid, cinnamic acid, salicylic acid, etc.

As used herein, "pharmaceutically acceptable carrier" comprises any standard pharmaceutically accepted carriers known to those of ordinary skill in the art in formulating pharmaceutical compositions. Thus, the antibodies or peptides, by themselves, such as being present as pharmaceutically acceptable salts, or as conjugates, may be prepared as formulations in pharmaceutically acceptable diluents, for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or as solid formulations in appropriate excipients.

The pharmaceutical compositions may further comprise one or more buffers (e.g., neutral buffered saline or phosphate buffered saline), carbohydrates (e.g., glucose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, adjuvants (e.g., aluminium hydroxide), solutes that render the formulation isotonic, hypotonic or weakly hypertonic with the blood of a recipient, suspending agents, thickening agents, and/or preservatives. Alternatively, compositions of the present invention may be formulated as a lyophilisate.

While any suitable carrier known to those of ordinary skill in the art may be employed in the compositions of this invention, the type of carrier will typically vary depending on the mode of administration.

For parenteral administration, the compositions can be administered as injectable dosages of a solution or suspension of the substance in a physiologically acceptable diluent with a pharmaceutical carrier that can be a sterile liquid such as sterile pyrogen free water, oils, saline, glycerol, polyethylene glycol or ethanol. Additionally, auxiliary substances, such as wetting or emulsifying agents, surfactants, pH buffering substances and the like can be present in compositions.

Other components of pharmaceutical compositions are those of petroleum, animal, vegetable, or synthetic origin, for example, non-aqueous solutions of peanut oil, soybean oil, corn oil, cottonseed oil, ethyl oleate, and isopropyl myristate. Antibodies can be administered in the form of a depot injection or implant preparation which can be formulated in such a manner as to permit a sustained release of the active ingredient. An exemplary composition may comprise antibody at 5 mg/ml, formulated in aqueous buffer consisting of 50 mM L-histidine, 150 mM NaCl, adjusted to pH 6.0 with HCl.

Typically, the compositions are prepared as injectables, either as liquid solutions or suspensions, or solid or powder forms suitable for reconstitution with suitable vehicles, including by way of example and not limitation, sterile pyrogen free water, saline, buffered solutions, dextrose solution, etc., prior to injection. The preparation also can be emulsified or encapsulated in liposomes or micro particles such as polylactide, polyglycolide, or copolymers, or other known encapsulating technologies.

The pharmaceutical compositions described herein may be presented in unit-dose or multi-dose containers, such as sealed ampules or vials. Such containers are typically sealed in such a way to preserve the sterility and stability of the formulation until use. In general, formulations may be stored as suspensions, solutions or emulsions in oily or aqueous vehicles, as indicated above.

Alternatively, a pharmaceutical composition may be stored in a lyophilized condition requiring only the addition of a sterile liquid carrier immediately prior to use.

Uses for Anti-CD63 Antibodies

The anti-CD63 antibodies of the invention have various utilities. In one embodiment, the anti-CD63 antibodies are useful for the affinity purification of exosomes. In this process, the antibodies against CD63 can be immobilized on a suitable support, such as a Sephadex resin or filter paper, using methods well known in the art. The immobilized antibody then is contacted with a sample containing the desired exosomes containing CD63 to be purified, and thereafter the support is washed with a suitable solvent that will remove substantially all the material in the sample except the exosomes which are bound to the immobilized antibody. Finally, the support can be washed with another suitable solvent that will release the exosomes from the antibody.

In another embodiment, provided is a method of treatment of a disease, such as cancer. The method of the invention preferably includes the step of providing an antibody or CD63 antigen-binding fragment thereof, as described above, to a subject requiring said treatment.

Methods of immunotargeting cancer cells using antibodies or antibody fragments are well known in the art. U.S. Pat. No. 6,306,393, for instance, describes the use of anti-CD22 antibodies in the immunotherapy of B-cell malignancies, and U.S. Pat. No. 6,329,503 describes immunotargeting of cells that express serpentine transmembrane antigens. Antibodies described herein (including humanized or human monoclonal antibodies or fragments or other modifications thereof, optionally conjugated to cytotoxic or other agents) can be introduced into a patient such that the antibody binds to cancer cells and mediates the destruction of the cells and the tumor and/or inhibits the growth of the cells or the tumor.

Without intending to limit the disclosure, mechanisms by which such antibodies can exert a therapeutic effect may include, for example, complement-mediated cytolysis, antibody-dependent cellular cytotoxicity (ADCC)1 modulating the physiologic function of the tumor antigen, inhibiting binding or signal transduction pathways, modulating tumor cell differentiation, altering tumor angiogenesis factor profiles, modulating the secretion of immune stimulating or tumor suppressing cytokines and growth factors, modulating cellular adhesion, and/or by inducing apoptosis.

The antibodies can also be conjugated to toxic, chemotherapeutic, or therapeutic agents, such as radioligands or cytosolic toxins, and may also be used therapeutically to deliver the toxic or therapeutic agent directly to tumor cells.

Treatment is meant to include therapeutic, prophylactic, palliative, or suppressive treatment for the disease, disorder or undesirable condition. Treatment encompasses administration of the subject antibodies in an appropriate form prior to the onset of disease symptoms and/or after clinical manifestations, or other manifestations, of the disease to reduce disease severity, halt disease progression, or eliminate the disease. Prevention of the disease includes prolonging or delaying the onset of symptoms of the disorder or disease, preferably in a subject with increased susceptibility to the disease.

The therapeutic preparations can use nonmodified antibodies or antibodies conjugated with a therapeutic compound, such as a toxin or cytotoxic molecule, depending on the functionality of the antibody. Generally, when nonmodified antibodies are used, they will typically have a functional Fc region. By "functional Fc region" herein is meant a minimal sequence for effecting the biological function of Fc, such as binding to Fc receptors, particularly FcγR (e.g., Fcγ RI, FcγRII, and Fcγ RIII).

Without being bound by theory, it is believed that the Fc region may affect the effectiveness of anti-tumor monoclonal antibodies by binding to Fc receptors immune effector cells and modulating cell mediated cytotoxicity, endocytosis, phagocytosis, release of inflammatory cytokines, complement mediate cytotoxicity, and antigen presentation. In this regard, polyclonal antibodies, or mixtures of monoclonals will be advantageous because they will bind to different epitopes and, thus, have a higher density of Fc on the cell surface as compared to when a single monoclonal antibody is used. Of course, to enhance their effectiveness in depleting targeted cells, or where nonmodified antibodies are not therapeutically effective, antibodies conjugated to toxins or cytotoxic agents may be used.

The antibody compositions may be used either alone or in combination with other therapeutic agents to increase efficacy of traditional treatments or to target abnormal cells not targeted by the antibodies. The antibodies and antibody compositions of the invention may include, for example, PEGylated antibodies and/or pretargeting constructs of the antibodies. Combining the antibody therapy method with a chemotherapeutic, radiation or surgical regimen may be preferred in patients that have not received chemotherapeutic treatment, whereas treatment with the antibody therapy may be indicated for patients who have received one or more chemotherapies. Additionally, antibody therapy can also enable the use of reduced dosages of concomitant chemotherapy, particularly in patients that do not tolerate the toxicity of the chemotherapeutic agent very well. Furthermore, treatment of cancer patients with the antibody with tumors resistant to chemotherapeutic agents might induce sensitivity and responsiveness to these agents in combination.

In one aspect, the antibodies are used adjunctively with therapeutic cytotoxic agents, including, by way of example and not limitation, busulfan, thioguanine, idarubicin, cytosine arabinoside, 6-mercaptopurine, doxorubicin, daunorubicin, etoposide, and hydroxyurea. Other agents useful as adjuncts to antibody therapy are compounds directed specifically to the abnormal cellular molecule found in the disease state. These agents will be disease specific.

The amount of the compositions needed for achieving a therapeutic effect will be determined empirically in accordance with conventional procedures for the particular purpose. Generally, for administering the compositions ex vivo or in vivo for therapeutic purposes, the compositions are given at a pharmacologically effective dose. By "pharmacologically effective amount" or "pharmacologically effective dose" is an amount sufficient to produce the desired physiological effect or amount capable of achieving the desired result, particularly for treating or retreating the disorder or disease condition, including reducing or eliminating one or more symptoms or manifestations of the disorder or disease.

As an illustration, administration of antibodies to a patient suffering from cancer provides a therapeutic benefit not only when the underlying disease is eradicated or ameliorated, but also when the patient reports a decrease in the severity or duration of the symptoms associated with the disease. Therapeutic benefit also includes halting or slowing the progression of the underlying disease or disorder, regardless of whether improvement is realized.

The amount administered to the subject will vary depending upon what is being administered, the purpose of the administration, such as prophylaxis or therapy, the state or condition of the subject, the manner of administration, the number of administrations, interval between administrations, and the like. These can be determined empirically by those skilled in the art and may be adjusted for the extent of the therapeutic response. Factors to consider in determining an appropriate dose include, but are not limited to, size and weight of the subject, the age and sex of the subject, the severity of the symptom, the stage of the disease, method of delivery, half-life of the antibodies, and efficacy of the antibodies. Stage of the disease to consider includes whether the disease is acute or chronic, relapsing or remitting phase, and the progressiveness of the disease. Determining the dosages and times of administration for a therapeutically effective amount is well within the skill of the ordinary person in the art.

For any compositions of the present disclosure, the therapeutically effective dose is readily determined by methods well known in the art. For example, an initial effective dose can be estimated from cell culture or other in vitro assays. For example, Sliwkowsky, M X et al. (1999) Semin. Oncol. 26.suppl. 12:60 describes in vitro measurements of antibody dependent cellular cytoxicity. A dose can then be formulated in animal models to generate a circulating concentration or tissue concentration, including that of the IC50 as determined by the cell culture assays.

In addition, the toxicity and therapeutic efficacy are generally determined by cell culture assays and/or experimental animals, typically by determining the LD50 (lethal dose to 50% of the test population) and ED50 (therapeutically effectiveness in 50% of the test population). The dose ratio of toxicity and therapeutic effectiveness is the therapeutic index. Preferred are compositions, individually or in combination, exhibiting high therapeutic indices. Determination of the effective amount is well within the skill of those in the art, particularly given the detailed disclosure provided herein. Guidance is also found in standard reference works, for example Fingl and Woodbury, General Principles In: The Pharmaceutical Basis of Therapeutics pp. 1-46 (1975), and the references cited therein.

To achieve an initial tolerizing dose, consideration is given to the possibility that the antibodies may be immunogenic in humans and in non-human primates. The immune response may be biologically significant and may impair the therapeutic efficacy of the antibody even if the antibody is partly or chiefly comprised of human immunoglobulin sequences, for example, in the case of a chimeric or humanized antibody. Within certain embodiments, an initial high dose of antibody is administered such that a degree of immunological tolerance to the therapeutic antibody is established. The tolerizing dose is sufficient to prevent or reduce the induction of an antibody response to repeat administration of the committed progenitor cell specific antibody.

Ranges for the tolerizing dose are, for example, between 10 mg/kg body weight to 50 mg/kg body weight, inclusive. In some embodiments, ranges for the tolerizing dose are between 20 and 40 mg/kg, inclusive. In still other embodiments, ranges for the tolerizing dose are between 20 and 25 mg/kg, inclusive.

Within these therapeutic regimens, the therapeutically effective dose of antibodies may be administered in the range of 0.1 to 10 mg/kg body weight, inclusive. In certain embodiments, therapeutically effective doses are in the range of 0.2 to 5 mg/kg body weight, inclusive. In other embodiments, therapeutically effective doses are in the range of 0.5 to 2 mg/kg, inclusive. Within alternative embodiments, the subsequent therapeutic dose or doses may be in the same or different formulation as the tolerizing dose and/or may be administered by the same or different route as the tolerizing dose.

Antibody compositions may be formulated for any appropriate manner of administration, including for example, oral, nasal, mucosal, intravenous, intraperitoneal, intradermal, subcutaneous, and intramuscular administration.

For the purposes of this invention, the methods of administration are chosen depending on the condition being treated, the form of the subject antibodies, and the pharmaceutical composition.

Administration of the antibody compositions can be done in a variety of ways, including, but not limited to, continuously, subcutaneously, intravenously, orally, topically, transdermal, intraperitoneal, intramuscularly, and intravesically. For example, microparticle, microsphere, and microencapsulate formulations are useful for oral, intramuscular, or subcutaneous administrations. Liposomes and nanoparticles are additionally suitable for intravenous administrations. Administration of the pharmaceutical compositions may be through a single route or concurrently by several routes. For instance, intraperitoneal administration can be accompanied by intravenous injections. Preferably the therapeutic doses are administered intravenously, intraperitonealy, intramuscularly, or subcutaneously.

The compositions may be administered once or several times. In some embodiments, the compositions may be administered once per day, a few or several times per day, or even multiple times per day, depending upon, among other things, the indication being treated and the judgment of the prescribing physician.

Administration of the compositions may also be achieved through sustained release or long-term delivery methods, which are well known to those skilled in the art. By "sustained release or" "long term release" as used herein is meant that the delivery system administers a pharmaceutically therapeutic amount of subject compounds for more than a day, preferably more than a week, and most preferable at least about 30 days to 60 days, or longer. Long term release systems may comprise implantable solids or gels containing the antibodies, such as biodegradable polymers described above; pumps, including peristaltic pumps and fluorocarbon propellant pumps; osmotic and mini-osmotic pumps; and the like.

The method of the invention contemplates the administration of single monoclonal antibodies and any antibody that recognizes the particular antigens recognized by these antibodies, as well as combinations, of different monoclonal antibodies. Two or more monoclonal antibodies may provide an improved effect compared to a single antibody. Alternatively, a combination of an antibody with an antibody that binds a different antigen may provide an improved effect compared to a single antibody. Such monoclonal antibodies cocktails may have certain advantages inasmuch as they contain monoclonal antibodies, which exploit different effector mechanisms or combine directly cytotoxic monoclonal antibodies with monoclonal antibodies that rely on immune effector functionality. Such monoclonal antibodies in combination may exhibit synergistic therapeutic effects.

In another embodiment, anti-CD63 antibodies may be used in diagnostic assays for CD63, e.g., detecting its expression in specific cells, tissues, or serum. Various diagnostic and prognostic assay techniques known in the art may be used, such as competitive binding assays, direct or indirect sandwich assays and immunoprecipitation assays conducted in either heterogeneous or homogeneous phases (Zola (1987) Monoclonal Antibodies: A Manual of Techniques, CRC Press, Inc. pp. 147-1581). The antibodies used in the assays can be labeled with a detectable moiety. The detectable moiety should be capable of producing, either directly or indirectly, a detectable signal. Any method known in the art for conjugating the antibody to the detectable moiety may be employed, including those methods described by Hunter et al. (1962) Nature 144:945; David et al. (1974) Biochemistry 13:1014; Pain et al. (1981) J. Immunol. Meth. 40:219; and, Nygren, J. (1982) Histochem. and Cytochem. 30:407.

"Detecting" refers to determining the presence, absence, or amount of an analyte in a sample, and can include quantifying the amount of the analyte in a sample or per cell in a sample.

"Diagnostic" refers to identifying the presence or nature of a pathologic condition. Diagnostic methods differ in their specificity and sensitivity. While a particular diagnostic method may not provide a definitive diagnosis of a condition, it suffices if the method provides a positive indication that aids in diagnosis.

"Immunoassay" refers to a method of detecting an analyte in a sample involving contacting the sample with an antibody that specifically binds to the analyte and detecting binding between the antibody and the analyte.

"Immunohistochemical" (abbreviated IHC) refers to specific binding agents, such as polyclonal and monoclonal antibodies, which recognize and mark antigens of interest, often by a chemical that shows that the agent has bound to the antigen of interest. An example of an IHC agent is a CD63 monoclonal antibody.

The present invention relates to diagnostic assays, both quantitative and qualitative for detecting levels of CD63 polypeptide in cells, tissues and bodily fluids, including determination of normal and abnormal levels. Assay techniques that can be used to determine levels of a polypeptide, such as CD63 of the present invention, in a sample derived from a host are well-known to those of skill in the art. Such assay methods include, but are not limited to, radioimmunoassays, immunohistochemistry assays, in situ hybridization assays, competitive-binding assays, Western Blot analyses and ELISA assays. Among these, ELISAs are frequently used to detect a gene's expressed protein in biological fluids. An ELISA assay initially comprises preparing an antibody specific to CD63, preferably a monoclonal antibody. In addition, a reporter antibody generally is prepared which binds specifically to CD63. The reporter antibody is attached to a detectable reagent such as a radioactive, fluorescent or enzymatic reagent, for example horseradish peroxidase enzyme or alkaline phosphatase.

The above tests can be carried out on samples derived from subjects' bodily fluids and tissue extracts (homogenates or solubilized tissue) such as from tissue biopsy and autopsy material. Levels of CD63, determined in cells and tissues from a patient suspected of suffering from cancer by measuring the polypeptide or by transcription levels, are compared to levels of CD63 in normal or control cells or tissues. Increased levels of CD63 measured in the subject as compared to levels in the same cells, tissues, or bodily fluids obtained from normal, healthy individuals are indicative of cancer. By "increased levels" it is meant an increase in measured CD63 levels in a subject as compared to CD63 levels in the same normal cells or tissues. Detection of increased CD63 levels is useful in the diagnosis of various cancers including, but not limited to, breast cancer, pancreatic cancer, prostate cancer, melanoma, colon cancer, lung cancer, and thyroid cancer.

Further, monitoring of CD63 levels in a subject diagnosed with cancer is useful in determining the onset of metastases in cancers that have not yet metastasized and in determining the stage of the cancer. For example, detection of CD63 can be used in a method of monitoring cancer in a subject that has not metastasized for the onset of metastasis. In this method, a subject suffering from a cancer that is not known to have metastasized is identified. CD63 levels in a sample from the subject are then measured. These measured CD63 levels are then compared with levels of CD63 from a normal control sample. An increase in measured CD63 levels in the subject versus the normal control is associated with a cancer that has metastasized.

The stage of cancer in a subject suffering from can also be determined. In this method a subject suffering from cancer is identified. CD63 levels in a sample of tissue from the patient are measured to establish a baseline CD63 level for said patient. CD63 levels in samples of the same tissue are then determined at subsequent time periods such as scheduled check-ups with the subject's physician. Measured CD63 levels are then compared with the baseline CD63 levels for the patient. In this method, an increase in measured CD63 levels in the subject versus baseline CD63 levels in the subject is associated with a cancer that is progressing and a decrease in measured CD63 levels versus baseline CD63 levels is associated with a cancer that is regressing or in remission. Increases in measured CD63 levels as compared to baseline CD63 levels established for the subject may also be indicative of metastases.

In one embodiment, CD63 immunohistochemistry functions as an "index diagnostic" to assign risk based on the presence of CD63 expression. Therefore, based on this and other parameters (e.g., size of lesion), one can determine whether or not different therapeutic modalities (i.e., chemotherapy, radiation therapy, surgery) should be used. In a related aspect, methods for monitoring progression of pre-malignancy into a malignant phenotype are disclosed. For example, by using serial sampling (i.e., biopsy) of the tissue and observing the state of CD63 expression in the lesions, one can determine whether or not the premalignancies are progressing in a way that would indicate whether therapeutic intervention is advised or is successful.

One aspect of the invention is a method to determine the likelihood of a group of cells to become cancerous, e.g., the cells or glands become premalignancies or progress to cancerous lesions. The invention utilizes an agent, such as an antibody, that specifically binds to CD63 protein to assess levels of CD63 in tissue and cells. CD63 expression in cells and tissue may also be assessed using nucleic acid analysis, such as selective amplification, or hybridization methods. A level of CD63 above normal or control levels, indicates an increased likelihood that premalignant disease is present, i.e., that the cells or tissues are premalignant.

Detection of CD63 can be combined with detection of one or more additional biomarkers of cancer. These biomarkers include by way of non-limiting example tissue inhibitor of metalloproteinase-1 (TIMP-1), EFNB1, ERCC1, HER2, VEGF, EGFR, AFRs, Rabs, ADAM10, CD44, NG2, ephrin-B1, MIF, b-catenin, Junction, plakoglobin, glalectin-4, RACK1, tetrspanin-8, FasL, TRAIL, A33, CEA, EGFR, dipeptidase 1, hsc-70, tetraspanins, ESCRT, TS, PTEN, TOPO1, EpCam, CD81, CD9, CD66, KIA1, intact fibronectin, PSA, TMPRSS2, FASLG, TNFSF10, PSMA, NGEP, IL-7R1, CSCR4, CysLT1R, TRPM8, Kv1.3, TRPV6, TRPM8, PSGR, MISIIR, PCSA, PSMA, and B7H3.

In certain embodiments, detection of CD63 alone or in combination with one or more additional biomarkers is used for the diagnosis and/or characterization of breast cancer, pancreatic cancer, prostate cancer, melanoma, colon cancer, lung cancer, or thyroid cancer with a high degree of sensitivity and/or specificity.

The cancer can be characterized and/or diagnosed using one or more processes disclosed herein with at least 60, 61, 62, 63, 64, 65, 66, 67, 68, 69, or 70% sensitivity. The cancer can be characterized and/or diagnosed with at least 80, 81, 82, 83, 84, 85, 86, or 87% sensitivity. For example, the cancer can be characterized and/or diagnosed with at least 87.1, 87.2, 87.3, 87.4, 87.5, 87.6, 87.7, 87.8, 87.9, 88.0, or 89% sensitivity, such as with at least 90% sensitivity, such as at least 91, 92, 93, 94, 95, 96, 97, 98, 99 or 100% sensitivity.

The cancer of a subject can also be characterized and/or diagnosed with at least 70, 71, 72, 73, 74, 75, 76, 77, 78, 79, 80, 81, 82, 83, 84, 85, 86, 87, 88, 89, 90, 91, 92, 93, 94, 95, 96, or 97% specificity, such as with at least 97.1, 97.2, 97.3, 97.4, 97.5, 97.6, 97.7, 97.8, 97.8, 97.9, 98.0, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, 99.9 or 100% specificity.

The cancer can also be characterized and/or diagnosed with at least 70% sensitivity and at least 80, 90, 95, 99, or 100% specificity; at least 80% sensitivity and at least 80, 85, 90, 95, 99, or 100% specificity; at least 85% sensitivity and at least 80, 85, 90, 95, 99, or 100% specificity; at least 86% sensitivity and at least 80, 85, 90, 95, 99, or 100% specificity; at least 87% sensitivity and at least 80, 85, 90, 95, 99, or 100% specificity; at least 88% sensitivity and at least 80, 85, 90, 95, 99, or 100% specificity; at least 89% sensitivity and at least 80, 85, 90, 95, 99, or 100% specificity; at least 90% sensitivity and at least 80, 85, 90, 95, 99, or 100% specificity; at least 95% sensitivity and at least 80, 85, 90, 95, 99, or 100% specificity; at least 99% sensitivity and at least 80, 85, 90, 95, 99, or 100% specificity; or at least 100% sensitivity and at least 80, 85, 90, 95, 99, or 100% specificity.

Furthermore, the confidence level for determining the specificity, sensitivity, or both, may be with at least 90, 91, 92, 93, 94, 95, 96, 97, 98, or 99% confidence.

Antibody Kits

Antibody kits are provided which contain the necessary reagents to carry out the assays of the present invention. The kit may include one or more compartments, each to receive one or more containers such as: (a) a first container comprising one of the components of the present invention described above; and (b) one or more other containers comprising one or more of the following: wash reagents, reagents capable of detecting presence of the antibody or peptide.

The containers allow the efficient transfer of reagents from one compartment to another compartment such that the samples and reagents are not cross-contaminated, and the agents or solutions of each container can be added in a quantitative fashion from one compartment to another.

The kit typically contains containers that may be formed from a variety of materials, such as glass or plastic, and can include for example, bottles, vials, syringes, and test tubes. A label typically accompanies the kit, and includes any writing or recorded material, which may be in electronic or computer readable form (e.g., disk, optical disc, or tape) providing instructions or other information for used of the contents of the kit. The label indicates that the formulation is used for diagnosing or treating the disorder of choice.

One skilled in the art will readily recognize that the disclosed antibodies of the present invention can be readily incorporated into one of the established kit formats that are well known in the art.

All patent and literature references cited in the present specification are hereby incorporated by reference in their entirety.

The following examples are offered for illustrative purposes only, and are not intended to limit the scope of the present invention in any way.

EXAMPLES

A murine hybridoma clone that secretes a murine monoclonal antibody to the human CD63 protein was generated. This antibody recognized human CD63 in its native form, which is expressed on lysosomes membranes and the cellular membrane. The LoVo colon cancer cell line was used to immunize mice, and screened using a recombinant CD63 extracellular domain fusion protein. Hybridoma clone, designated Z63.5 and having ATCC accession number PTA-120178, was produced and identified using the materials and methods described in detail below. Z63.5 secretes an antibody recognizing CD63. The antibody is of a murine IgG1, kappa chain isotype.

Commercially available reagents referred to in the examples were used according to manufacturer's instructions unless otherwise indicated.

Example 1

Hybridoma Production and Screening—mAb Z63.5

Below are the protocols used for hybridoma production for Fusion FX58, general hybridoma production used in the laboratory, as well as protocols used for screening and subcloning. The final hybridoma clone, mAb Z63.5, was a result of two subclonings.

A. Fusion FX58

4 Days Prior to Fusion

1) Two T-75 flasks of P3×653 cells were set up at about $5 \times 10^5$ cell/ml (50 ml) in C-DMEM and re-fed with fresh media added the day before fusion.

2) Which splenocyte sample to be used for fusion was determined: Splenocytes from mouse 34.1 (immunized with Fixed LoVo Cells).

Day of the Fusion

3) Fusion Media was prepared as follows:

| | |
|---|---|
| DMEM (LTI) | 128 ml |
| HAT (50X; Sigma) | 4 ml |
| OPI (100X: Sigma) | 2 ml |
| HEPES (1M; Sigma) | 2 ml |
| Glutamax II (100X; LTI) | 2 ml |
| NCTC (Sigma) | 20 ml |
| FBS (LTI) | 40 ml |
| Pen/Strep (LTI) | 2 ml |
| Nutridoma (BM) | 2 ml (added at 7) |

4) P3 cells were counted; $2 \times 10^8$ cells were pelleted and resuspend in 10 ml DMEM/HEPES.

5) Splenocytes from Mice 34.1 were thawed and a suspension prepared therefrom placed in a 15 ml conical tube. The cells were washed with 10 ml of warm DMEM/HEPES.

6) After washing, both P3 cells and splenocytes with 10 ml of DMEM/HEPES, both P3 and splenocytes were taken up in 5 ml each of warm DMEM/HEPES and mixed in a 14 ml round bottom tube. Cells were pelleted and all of the supernatant was removed with a pipet. The pellet was disrupted gently and placed at 37° C.

7) One ml of 50% PEG/DMSO (Sigma) at 37° C. was added over 45-60 seconds with constant stirring. After 45 seconds of swirling, 2 ml of warm DMEM/HEPES/5% DMSO was added over 2 minutes in the same manner as the PEG. Next, 8 ml of DMEM/HEPES/DMSO was added over 2 minutes. Fused cells were incubated 15 minutes at 37° C.

8) Spleen cells from the normal mice were resuspended in 160 ml of fusion medium and 100 µl was added into eight 96-well flat-bottom plates (for two fusions).

9) The fused cells were pelleted and resuspended in 160 ml of fusion medium with Nutridoma freshly added.

10) Two-hundred µl per well was added of cell suspension to eight 96-well plates.

11) The eight fusion plates were placed in a plastic container and the container was placed in an incubator with 5% $CO_2$ at 37° C.

B. General Hybridoma Fusion Protocol

Fusion Preparation:

3-4 Days Prior to Fusion

1) Two T-75 or one T-225 flask of P3×653 at $4×10^5$ cell/ml (30 ml) in 10% HY (or C-DMEM) were set up. Fresh media was added the day before fusion.
2) The mice were boosted for fusion with i.v. injection.
3) Dissecting equipment was autoclaved.

Day of the Fusion

| 4) | Fusion Media was prepared as follows: | DMEM (LTI) | 128 ml |
|---|---|---|---|
| | | HAT (50X; Sigma) | 4 ml |
| | | OPI (100X: Sigma) | 2 ml |
| | | HEPES (1M; Sigma) | 2 ml |
| | | Glutamax I (100X; LTI) | 2 ml |
| | | NCTC (Sigma) | 20 ml |
| | | FBS (LTI) | 40 ml |
| | | Pen/Strep (LTI) | 2 ml |
| | | Nutridoma (BM) | 1.6 ml |

5) Fifty ml of SF-DMEM with 0.5 ml of 1 M HEPES=>DMEM/HEPES was prepared.
6) Nine and one-half ml of DMEM/HEPES were removed into 15 ml conical and 0.5 ml DMSO=>DMEM/HEPES/DMSO added.
7) The following were placed in 37° C. water bath: 200 ml Fusion Media (FX-media)
  40 ml DMEM/HEPES
  10 ml DMEM/HEPES/DMSO
  1 ml vial PEG/DMSO
8) Eight flat bottom 96 well plates were labeled with fusion number, plate number and date (example: FX03.5 8/31/07) 50×HAT: Resuspend one bottle in 10 mL of SF-DMEM 100×OPI: Resuspend one bottle in 10 mL Sterile Water C. Fusion Fusion Culture (See FIG. 1 for Illustration of Fusion Steps).
1) Mice were sacrificed and spleens removed. Each spleen was placed in 10 ml DMEM/HEPES in 100 mm cell culture dish, grown and P3 cells counted; $5-20×10^7$ cells were used.
2) The splenocytes were removed by teasing the spleen.
3) The resulting splenic cell suspension was placed in a 15 ml conical tube and large debris allowed to settle for 2-3 minutes. P3 cells were then transferred to 50 ml conical tube.
4) Cell suspension was removed into new 15 ml conical tube and pellet cells by centrifugation and P3 cells pelleted by centrifugation.
5) Splenocyte was washed with 10 ml of warm DMEM/HEPES (when resuspending, clots allowed to stick to pipet).
6) P3 cells were resuspended and washed in 10 ml DMEM/HEPES.
7) After pelleting P3 cells and splenocytes, they were resuspended in 5 ml each of warm DMEM/HEPES and mixed in a 14 ml round bottom tube (Falcon 2059).
8) The cells were pelleted and all of the supernatant removed by aspiration.
9) The pellet was gently disrupted and incubated at 37° C. for 1-2 minutes.
10) One ml of 50% PEG/DMSO (Sigma) was added over 45-60 seconds with constant stirring and flicking.
11) The mixture was then swirled at 37° C. for 45 seconds.
12) The PEG was diluted out by adding 2 ml of warm DMEM/HEPES/5% DMSO over 2 minutes in the same manner as the PEG.
13) The mixture was further diluted by adding 8 ml of DMEM/HEPES/DMSO over 2 minutes.
14) The fused cells were incubated for 15 minutes at 37° C.
15) Fused cells were pelleted and resuspended in 160 ml of fusion medium with Nutridoma freshly added.
16) The mixture was plated at 200 µl/well and incubated in a plastic container at 37° C.

D. Screening of FX58

Primary Screen

1) Two 384-well plates were coated with 25 µl per well of approximately 0.5 µg/ml GST-CD63 in coating buffer (50 mM Tris-Cl, pH 9.5).
2) Incubated overnight at 4° C.

Day of the Screening

3) Coating protein was removed and 50 µl per well of blocking buffer (1% BSA) added. Incubated for 30 min at 37° C.
4) Added 25 µl of each well from the fusion and incubated for 1 hr at room temperature (RT).
5) Washed 3× with 50 µl/well of PBS-T.
6) Added 25 µl to each well of 1 µg/ml HRP-GAM Fc in PBS-T. Incubated for 1 hr at RT.
7) Washed 3× with 50 µl/well of PBS-T.
8) Add 25 µl to each well of OPD substrate (Pierce) with 0.1% hydrogen peroxide. Incubated for 15 min at RT.
9) Added 25 µl to each well of STOP buffer (2 M sulfuric acid).
10) Read plates for absorbance at 495 nM.
11) Analyzed data using 384-well excel spreadsheet to determine positive hybridomas.

The raw data from the hybridoma ELISA screening plates 1-8 using binding GST-CD63 are shown in FIGS. 2-5. Overall, supernatant from 768 wells were screened for binding to GST-CD63. The data from two 384 well ELISA plates corresponding to eight 96-well hybridoma plates are shown. Highlighted wells from the 96-well plate show selected wells for expansion. Positive controls were put in wells A1 and A2 of the two 384-wells screening plates, respectively.

Figure 6:
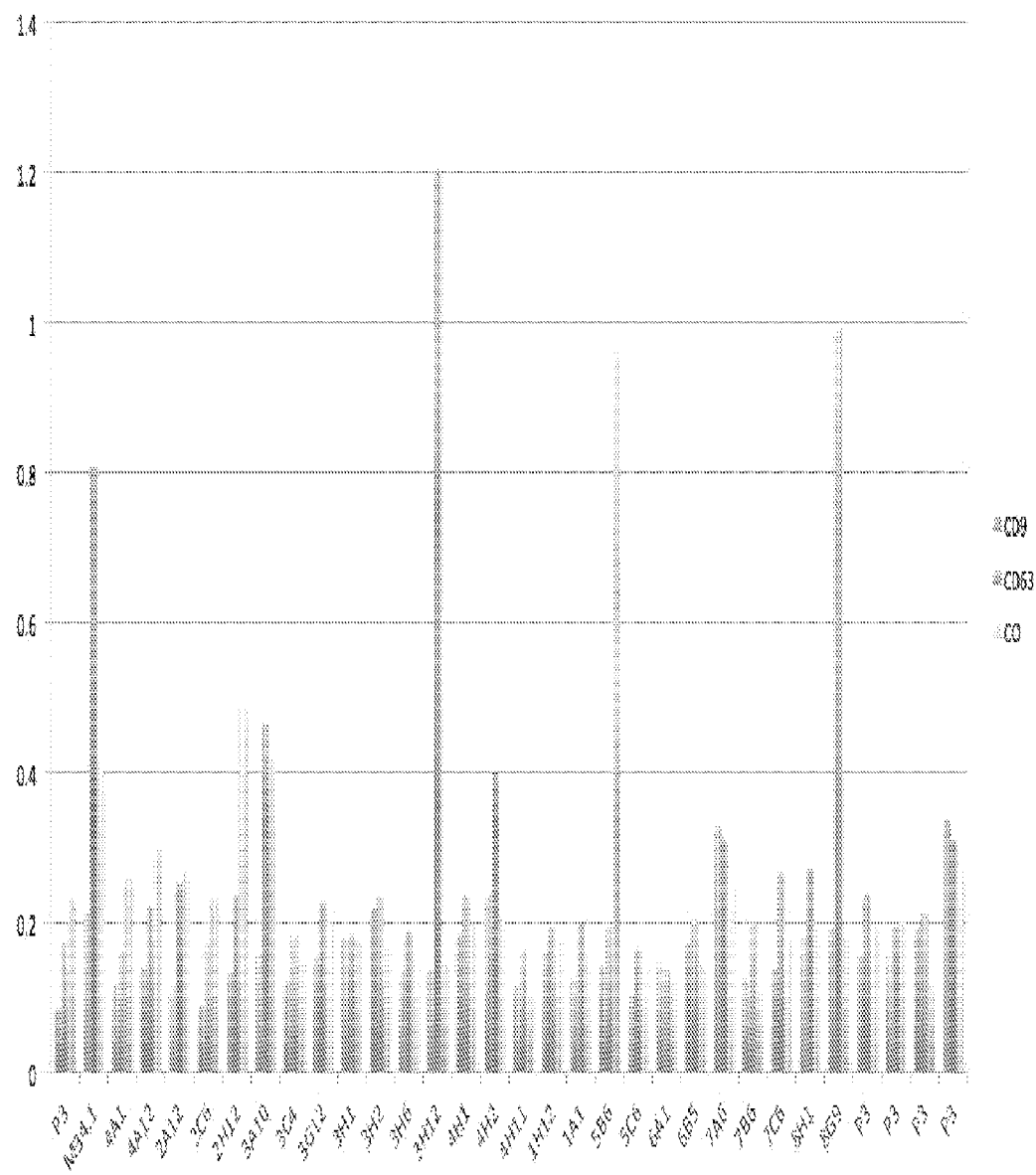
FIG. 6 shows the raw data and plot for the ELISA of binding of supernatant of parental clones to GST-CD9, GST-CD63 and GST-CO (TSPAN8). Two clones 3H12 and 8G9 were positive for CD63 and one 5B6 for TSPAN8. These clones were subsequently subcloned for single clone isolation and characterization.

Furthermore, the raw data and plot for the ELISA of binding of supernatant of parental clones to GST-CD9, GST-CD63 and GST-CO (TSPAN8) are shown in FIG. 6. Two clones 3H12 and 8G9 were positive for CD63 and one 5B6 for TSPAN8. These clones were subsequently subcloned for single clone isolation and characterization.

E. Limiting Dilution

20-HT Media (1st Limiting Dilution)
20-HY Media (2nd Limiting Dilution)
1) Added 100 µl of media to a clear, flat-bottom 96-well plate per clone.
2) Added 100 µl of hybridoma to well A1 and mix.
3) Transferred 100 µl from well A1 to well B1 serially diluting down to well H1.
4) Added 100 µl of media to column 1 totaling 200 µl in wells.
5) Used 8-channel pipet, transferred 100 µl from column 1 to column 2 (serially diluting down to column 12).
6) Added 100 µl of media to plates totally 200 µl in all wells.
7) Grew plates for 7-10 days before screening.

Results

The overall development of the final hybridoma clones, including response in screening assays for the parental, daughter and granddaughter clones from the limiting dilutions experiments, is summarized in FIG. 7. Final clones have a fusion identification ID and a designation name as shown.

F. Western Blot Analysis

Figure 8:
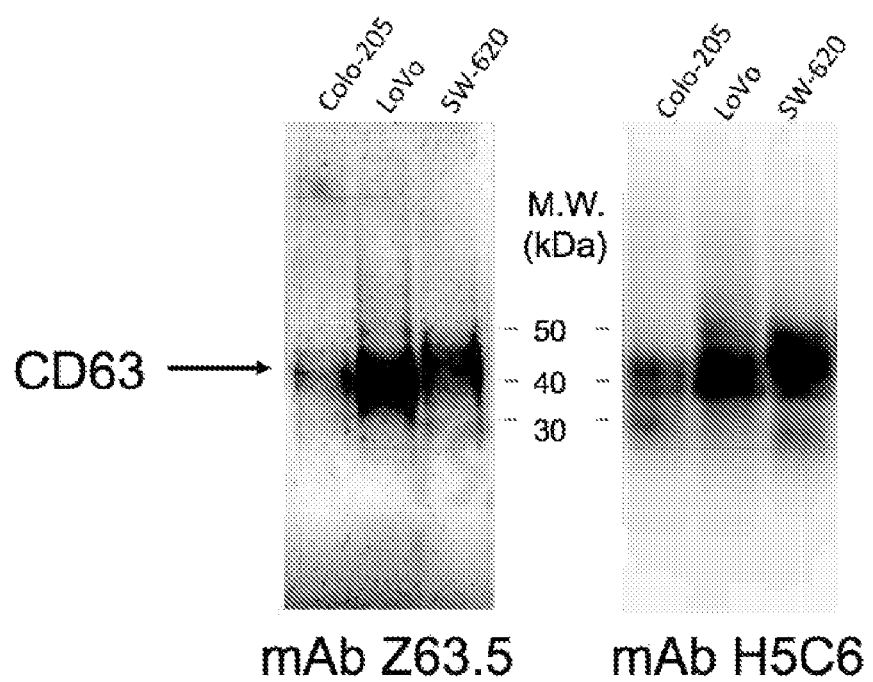
FIG. 8 shows the results of a western blot analysis using the monoclonal antibody of the invention (mAb Z63.5) indicating recognition of the CD63 protein from three colon cancer cell lines. The band recognized by mAb Z63.5 is similar to bands recognized by the anti-CD63 mAb H5C6.

A western blot analysis using the monoclonal antibody of the invention, (mAb Z63.5) was done indicating recognition of the CD63 protein from three colon cancer cell lines, as shown in FIG. 8. Standard procedures well known to those skilled in the art were used. The band recognized by mAb Z63.5 is similar to bands recognized by the anti-CD63 mAb H5C6.

Example 2

Western Blots of CD63 in Lysates from Exosomes

Figure 9:
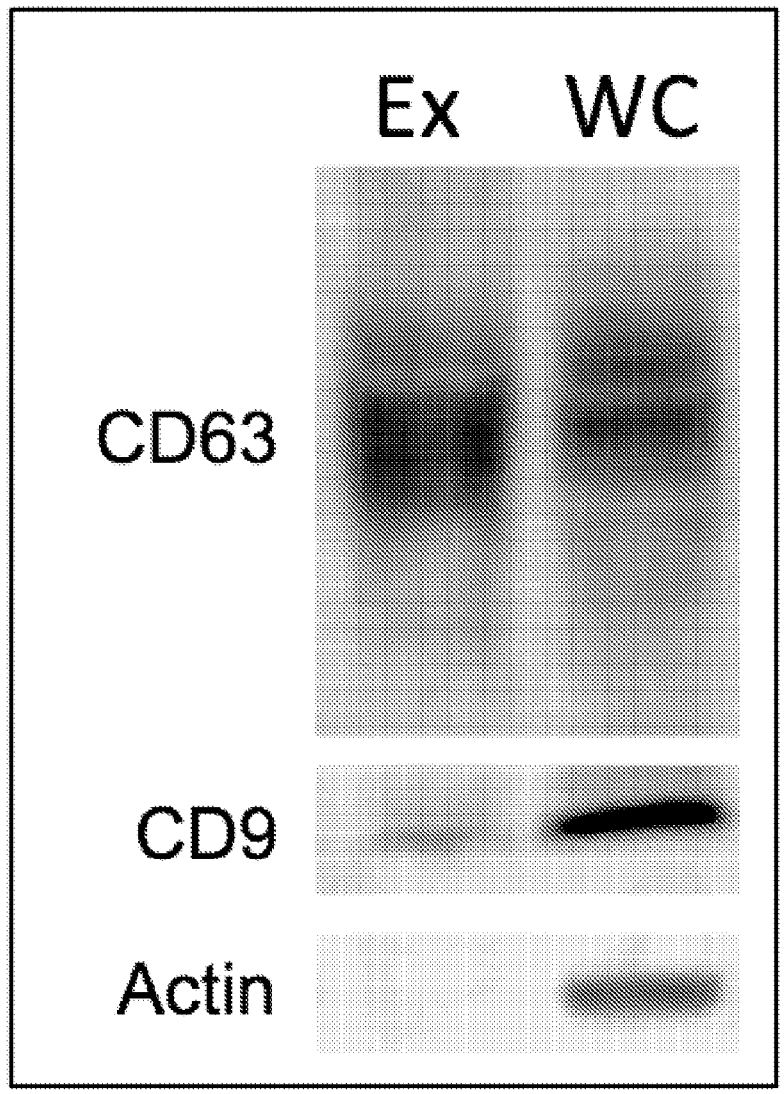
FIG. 9 shows expression of CD63 on exosomes. The Western blot shows staining for the exosomal markers CD63 and CD9 in lysates from exosomes (Ex) or whole cell lysates (WC) from LoVo colon cancer cells.

Lysates from exosomes (Ex) isolated from LoVo colon cancer cells or whole cell lysates (WC) were analyzed by immunoblotting for expression of CD63 using mAb H5C6, CD9 using mAb ALMA.1 and Actin using an anti-actin polyclonal antibody. Both CD63 and CD9 are known exosomal markers, and Actin is found only in cellular lysates. The data presented in FIG. 9 demonstrate the abundant expression of CD63 on exosomes and highlight the usefulness of the mAb Z63.5 in exosome purification.

Deposit of Biological Material

The following biological material has been deposited under the terms of the Budapest Treaty with the American Type Culture Collection (ATCC®), 10801 University Boulevard, Manassas, Va. 20110, and given the following accession number:

| Deposit | Accession Number | Date of Deposit |
|---|---|---|
| Murine hybridoma; Z63.5 | PTA-120178 | Apr. 3, 2013 |

The hybridoma cell line has been deposited under conditions that assure that access to the culture will be available during the pendency of this patent application to one determined by the Commissioner of Patents and Trademarks to be entitled thereto under 37 C.F.R. §1.14 and 35 U.S. C. §122. The deposit represents a substantially pure culture of the deposited hybridoma cell line. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

Having herein set forth the various embodiments of the present invention, it is anticipated that suitable modifications can be made thereto which will nonetheless remain within the scope of the invention. The invention shall therefore only be construed in accordance with the following claims below.

What is claimed is:

1. An isolated antibody that binds to a human CD63 protein, wherein the antibody is produced by a hybridoma cell line having ATCC accession number PTA-120178 and the antibody recognizes a CD63 protein from at least one colon cancer cell line.

2. An antigen-binding fragment of the antibody of claim 1 that binds to a native sequence CD63 polypeptide.

3. An anti-CD63 monoclonal antibody produced by a hybridoma cell line having ATCC accession number PTA-120178.

4. The antibody of claim 3, wherein the antibody is an IgG1, kappa chain isotype.

5. An antigen-binding fragment of the antibody of claim 3 that binds to a CD63 protein and wherein said antibody or antigen-binding fragment thereof binds a neoplastic cell or antigen thereof.

6. A method of purifying exosomes in human cell samples or body fluid, said method comprising the step of purifying an exosome preparation from the human cell sample or body fluid using the antibody of claim 3, wherein the exosomes have CD63 expressed thereon.

7. A method for detecting CD63 comprising the steps of:
    reacting a monoclonal antibody produced by a hybridoma cell line having ATCC accession number PTA-120178; and
    detecting a level of CD63 protein in the sample, wherein the sample collected from the subject is at least one sample selected from the group consisting of a tissue sample, a blood sample, a serum sample, and a plasma sample.

8. The method according to claim 7, wherein the monoclonal antibody is labeled.

9. The method according to claim 7, wherein the monoclonal antibody is labeled with one or more labels selected from the group consisting of a biotin label, a fluorescent label, an enzyme label, a coenzyme label, a chemiluminescent label, and a radioactive isotope label.

10. The antibody of claim 1 and further comprising a label.

11. The antibody of claim 10, wherein the label is selected from the group consisting of a biotin label, a fluorescent label, an enzyme label, a coenzyme label, a chemiluminescent label, and a radioactive isotope label.

12. The antibody of claim 3 and further comprising a label.

13. The antibody of claim 12, wherein the label is selected from the group consisting of a biotin label, a fluorescent label, an enzyme label, a coenzyme label, a chemiluminescent label, and a radioactive isotope label.

14. The antigen-binding fragment of claim 5 further comprising a label.

15. The antigen-binding fragment of claim 14, wherein the label is selected from the group consisting of a biotin label, a fluorescent label, an enzyme label, a coenzyme label, a chemiluminescent label, and a radioactive isotope label.

* * * * *